United States Patent [19]
Oshima et al.

[11] Patent Number: 5,699,786
[45] Date of Patent: Dec. 23, 1997

[54] ATOMIZER SYSTEM

[75] Inventors: Hironobu Oshima; Hiroyuki Matumori, both of Gunma, Japan

[73] Assignee: Sanyo Electric Co., Ltd., Moriguchi, Japan

[21] Appl. No.: 739,966

[22] Filed: Oct. 30, 1996

[30]     Foreign Application Priority Data

Oct. 31, 1995  [JP]  Japan .................. 7-305256
Feb. 29, 1996  [JP]  Japan .................. 8-067507

[51] Int. Cl.$^6$ .................................................. A61M 11/00
[52] U.S. Cl. .................. 128/200.21; 128/200.23; 128/200.14; 128/203.12
[58] Field of Search ............... 128/200.21, 200.22, 128/200.11, 200.14, 200.23, 202.13, 203.12, 204.18, 205.12, 205.27, 205.29

[56]     References Cited

U.S. PATENT DOCUMENTS

| | | | |
|---|---|---|---|
| 422,802 | 3/1890 | Kennedy | 128/200.11 |
| 1,897,378 | 2/1933 | Hinkle | 128/200.21 |
| 3,068,856 | 12/1962 | Bird et al. | 128/203.12 |
| 3,301,255 | 1/1967 | Thompson | 128/200.21 |
| 3,379,194 | 4/1968 | Ziermann | 128/200.21 |
| 3,502,077 | 3/1970 | Joseph | 128/200.14 |
| 4,267,974 | 5/1981 | Kienholz et al. | 128/200.21 |
| 4,330,088 | 5/1982 | Koyama et al. | 239/318 |
| 4,461,425 | 7/1984 | Miller | 239/338 |
| 4,467,796 | 8/1984 | Beagley | 128/202.13 |
| 4,823,784 | 4/1989 | Bordoni et al. | 128/200.21 |
| 4,977,634 | 12/1990 | Koji | 128/205.27 |
| 5,143,060 | 9/1992 | Smith | 128/205.12 |
| 5,144,945 | 9/1992 | Nishino et al. | 128/205.12 |
| 5,179,982 | 1/1993 | Berube et al. | 141/20 |
| 5,280,784 | 1/1994 | Kohler | 128/200.21 |
| 5,318,015 | 6/1994 | Mansson et al. | 128/200.22 |
| 5,396,885 | 3/1995 | Nelson | 128/204.18 |
| 5,479,920 | 1/1996 | Piper et al. | 128/204.18 |
| 5,570,682 | 11/1996 | Johnson | 128/203.12 |

FOREIGN PATENT DOCUMENTS

| | | | |
|---|---|---|---|
| WO 91/08839 | 6/1991 | European Pat. Off. . | |
| A-2 698 341 | 5/1994 | France . | |
| 1616190 | 8/1978 | Germany | 128/200.21 |
| A-632 423 | 10/1982 | Germany . | |

*Primary Examiner*—Vincent Millin
*Assistant Examiner*—V. Srivastava
*Attorney, Agent, or Firm*—Armstrong, Westerman, Hattori, McLeLand & Naughton

[57]     ABSTRACT

An atomizer system has a first pressure accumulation tank 7 for storing high-pressure air generated by a compressor 6, to which a second pressure accumulation tank 28 is connected via an air tube 3, so that the second tank 28 is charged with the high pressure air. The tube 3 has a sealing valve 26 which is removably connected with the second tank 28. The tank 28 is connected to a regulator which may reduce the pressure of the air supplied from the second tank 28 to a predetermined low pressure level. With the second tank 28 disconnected from the first tank 6, the low-pressure air is provided to an atomizer 11 for atomization of medicine in inhalation treatment.

**12 Claims, 17

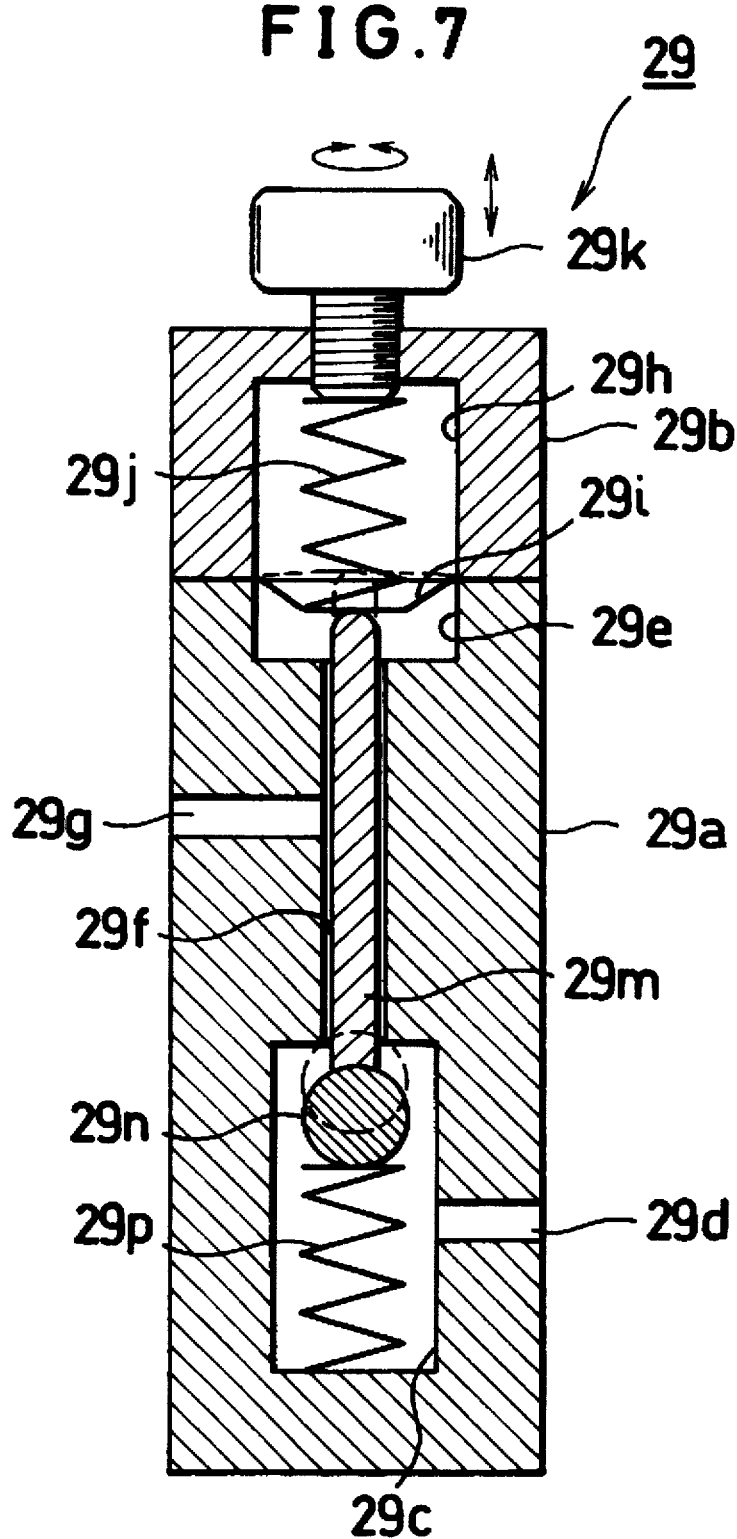

1

ATOMIZER SYSTEM

FIELD OF THE INVENTION

This invention relates to an atomizer system having a main unit and an atomizer connected directly or indirectly with the main unit via a portable unit and, more particularly, to an atomizer system for ejecting atomized liquid particles from the atomizer.

KNOWN ART

Conventional atomizer systems for use as an inhaler, for example, for the treatment of respiratory illness, generate atomized inhalants by means of pressurized air supplied by an air compressor.

However, this type of inhaler has a problem that the operation of an atomizer causes other patients to be disturbed by annoying noises and vibrations generated by the compressor. Since patients having respiratory illness are often afflicted with fits at midnight, use of such atomizer is then a serious problem to others sharing the room with that patient.

Another problem is that, if such atomizer system is installed at a remote place i.e. at a corner of the patient's room or a separate room away from the patient's room, the patient is required to move from his bed to the atomizer for treatment, which is often inconvenient and sometimes difficult for him, especially when he is critically ill. Such inconvenience or difficulty can even cause a serious problem if it takes time to transport the critically ill patient to the remote atomizer and results in delay in treatment.

Another problem pertinent to conventional atomizer systems is that they have a rather small number of air outlets for atomizers, so that patients must waste time waiting for treatment and that nurses are kept busy in resetting or cleaning each atomizer for the next patient. These are sources of inefficiency in hospitals. Furthermore, it takes some time even for a skilled nurse to set an atomizer at an optimum pressure for every patient. Thus, conventional systems are not convenient for most of the users.

A further problem is encountered in most of the conventional systems that an air filter used to clean the air for the atomizer has been often choked after long use, thereby failing to provide clean air to the patient. This can happen because it is difficult to tell when the filter has been choked and lost its filtering ability, thus resulting in a delay caused by the need for replacement of the filter by a new one.

The invention is aimed to overcome these disadvantages pertinent to conventional atomizer systems. It is therefore an object of the invention to provide an improved atomizer which may operate without any electric power and hence without noises nor vibrations.

It is another object of the invention to provide a movable compact atomizer system which is yet capable of providing a multiplicity of patients with inhalation atomizers.

It is still another object of the invention to provide an atomizer system equipped with a filter unit whose filtering ability is detectable, so that the filter unit may be replaced in an easy manner when it is contaminated, thereby providing a clean and safe atomizer system.

It is a further object of the invention to provide a structurally simple atomizer system having a multiplicity of air outlets adapted to provide optimum air pressures to a multiplicity of atomizers respectively connected with the air outlets, thereby providing convenient and efficient means for simultaneous treatment of multiple patients.

SUMMARY OF THE INVENTION

To this end, in one aspect of the invention, there is provided an atomizer system comprising: a main unit which includes an air compressor for generating high-pressure air, a first pressure accumulation tank for storing a volume of high-pressure air generated by the compressor, and at least one air tube for leading the high-pressure air from the pressure accumulation tank to an air outlet; and a portable unit which includes at least one sealing valve which is removably mounted on the air tube, a second pressure accumulation tank for accepting the air fed by the air tube, a regulator for decompressing the high-pressure air stored in the second pressure accumulation tank to reduce the pressure thereof and to generate low-pressure air having a predetermined pressure, and at least one atomizer for atomizing liquid by means of the low-pressure air.

Advantageously, this type of atomizer system has a compact portable unit which operates calmly and hence can be used anywhere, at any time in a hospital without bothering other patients. Since the portable unit includes a regulator which provides air at a constant low pressure, the system may generate inhalation medicine to a patient in a stable condition. The second pressure accumulation tank of the portable unit may hold a required amount of air required for a prolonged operation of the unit, thereby providing a portable atomizer having small dimensions.

Preferably the atomizer is removably mounted on the regulator via the valve and the air tube, so that when the system is used for one patient, only the atomizer needs to be replaced for sterilization, thereby maintaining required sanitary conditions.

A filter unit may be mounted in the main unit for cleaning the high-pressure air released from the first pressure accumulation tank, allowing the second pressure accumulation tank to be charged with the clean air for the atomizer. This is helpful for inhalation treatment since harmful components are removed from the air. The filter unit is removably mounted for easy replacement thereof.

The portable unit preferably has a shape of enclosed short upright cylinder serving as the second pressure accumulation tank, and is equipped with an atomizer and a regulator mounted on the top of the second pressure accumulation tank. Such short cylindrical configuration is desirable in that it has stability against an accidental engagement of the unit by a patient. The bottom of the tank is preferably removable so that the tank may be disassembled for cleaning.

The filter unit preferably includes different types of filters for filtering different kinds of contaminants, each filter having an indicator indicating if it is choked with contaminants or not. Also, the filter unit preferably has a mounting plate for mounting thereon the filters in series. The mounting plate has an observation window for monitoring the indicators.

With this type of filter unit, various kinds of contaminants may be removed if the filters are appropriately chosen, and it is easy to monitor the conditions of the filters by observing their changes in color for example, through the observation window. If the filters are determined to be replaced by observation, they may be replaced easily without delay by replacing the whole unit.

The filters mentioned above preferably include a dust filter for removing dust in the air, an oil mist filter for removing oily components, and an odor filter for removing bad odors. With these filters not only dust and odors but also oil particles from a machinery section of the system, for example, may be removed from the air, thereby improving the purity of the air and hence the quality of inhalation treatment.

In another aspect of the invention, there is provided an atomizer system comprising: a movable main unit which includes an air compressor for generating high-pressure air, a pressure accumulation tank for storing a volume of high pressure air generated by the compressor, at least one regulator for reducing the pressure of said high-pressure air in the first pressure accumulation tank to a predetermined low pressure, a multiplicity of air outlets communicating with the regulator for delivering the low-pressure air stored in the regulator, and a multiplicity of valves mounted in said air outlets, one for each air outlet, for controlling the flow of air that passes through said air outlets; and at least one atomizer to be connected with one of said air outlets via an air tube, for atomizing liquid by means of said low-pressure air.

This type of atomizer system may simultaneously treat many patients efficiently, since it has multiple air outlets, which is advantageous not only to the patients but also nurses for the reasons discussed in detail later.

A removable air filter unit may be provided in the main unit for cleaning the high-pressure air released from the pressure accumulation tank, so that clean air may be supplied from the air outlets. This helps to improve the inhalation treatment since the air gets rid of hazardous materials.

The atomizer system may be provided with a timer which is capable of controlling the individual valves so that the low-pressure air is supplied from the air outlets for only prescribed periods of time. This timer permits hospital personnel e.g. nurses, to set treatment periods for individual patients, thereby relieving the burden of the personnel and improving efficiency of the treatments.

The filter unit may contain different types of filters for filtering different contaminants, each filter having an indicator for indicating if it is choked with the contaminants or not. The filter unit has preferably a mounting plate for mounting thereon the filters in series and an observation window for monitoring the indicators.

With this type of filter unit various kinds of contaminants may be removed if the filters are appropriately chosen, and it is easy to monitor the conditions of the filters by observing their changes in color for example, through the observation window. If the filters are determined to be replaced by observation, they may be replaced easily without delay by replacing the whole unit.

The filters mentioned above preferably includes a dust filter for removing dust in the air, an oil mist filter for removing oily components, and an odor filter for removing bad odors. With these filters not only dust and odors but also oil particles from a machinery section of the system for example may be removed from the air, thereby improving the purity of the air and hence the quality of inhalation treatment.

Each of the air outlets may be provided with a regulator capable of regulating the pressure of the air released from the air outlet. Thus, the atomizer system may provide atomizers operating at optimum conditions for individual patients.

BRIEF DESCRIPTION OF THE DRAWINGS

These and other features of the present invention may be more readily understood by reference to the following description, taken in conjunction with the accompanying drawings, in which:

FIG. 7 is a cross sectional view of a regulator for use in the portable unit shown in FIG. 6B;

DETAILED DESCRIPTION OF THE PREFERRED EMBODIMENT

Figure 1:
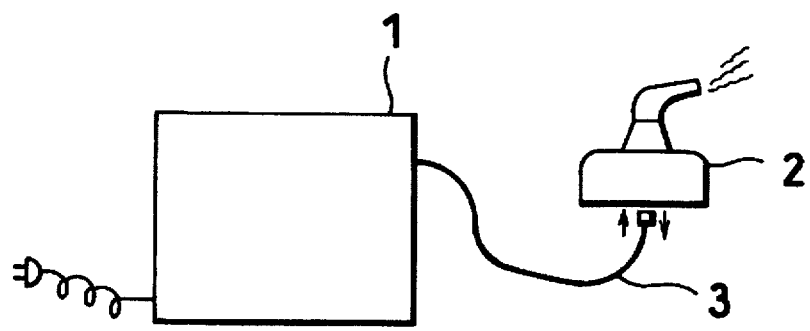
FIG. 1 is a schematic view of a first atomizer system according to the invention.

Referring now to FIG. 1, there is shown an atomizer system of the invention, which is intended for use as an inhalator for treating a patient having respiratory illness by having the patient inhale atomized medicine.

As seen in FIG. 1, the system includes a main unit 1 for generating clean high-pressure air, and a portable unit 2 which may store the high-pressure air and generate atomized medicine by the high-pressure air. The high-pressure air in the main unit 1 is supplied to the portable unit 2 through an air tube 3 which extends from the main unit 1 and is removably connected with the portable unit 2 following charging of the portable unit with high pressure air from the main unit.

Figure 2:
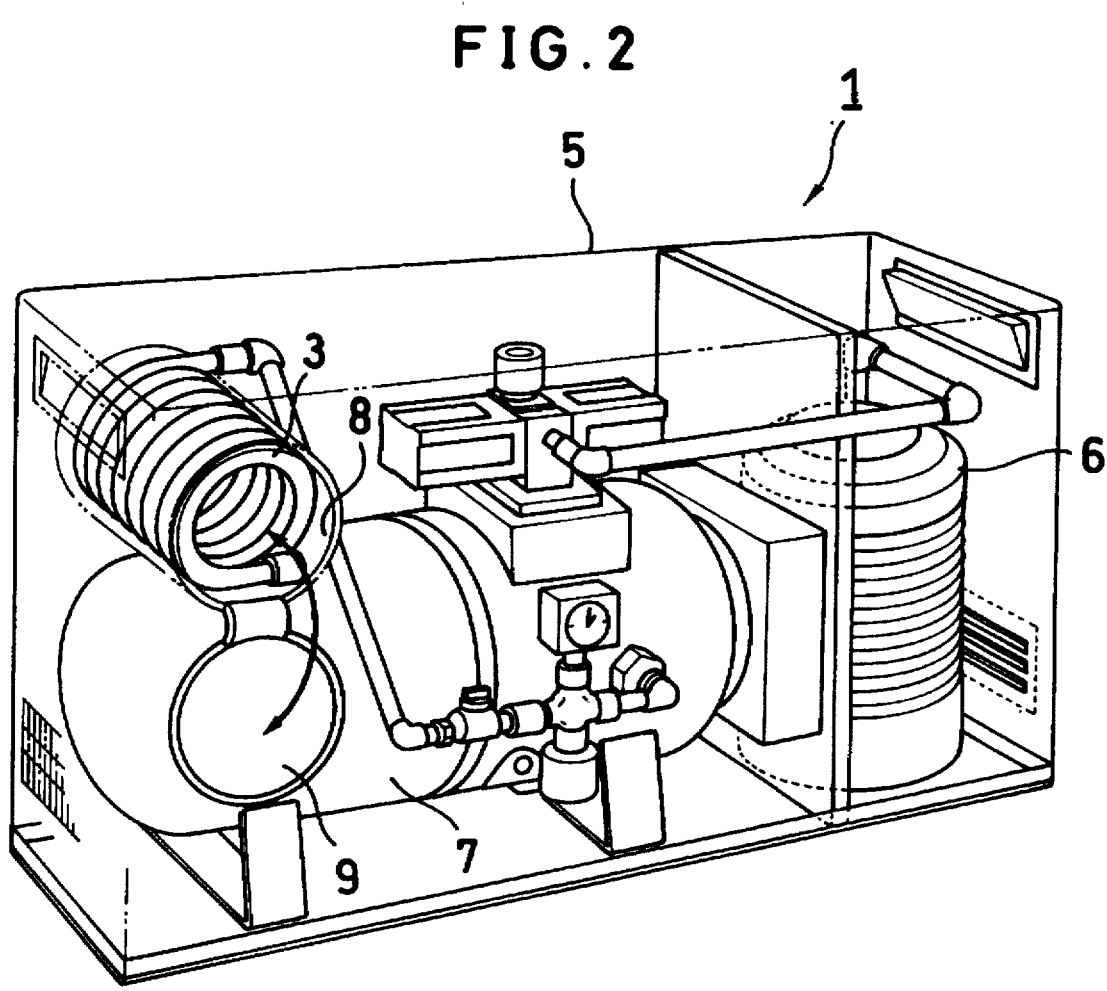
FIG. 2 is a perspective view of a main unit of the atomizer system shown in FIG. 1.

Referring to FIG. 2, there is shown a detailed arrangement of the main unit 1. The main unit 1 has a housing 5, which includes in the right side thereof a small chamber for accommodating a compressor 6 for generating the high-pressure air. In a large chamber at the left side of the housing 5 is a main tank 7 for storing the high-pressure air generated by the compressor 6.

A container 8 is provided above the main tank 7 for accommodating therein the air tube 3. The container 8 has a lid 9 for closing the container.

Figure 3:
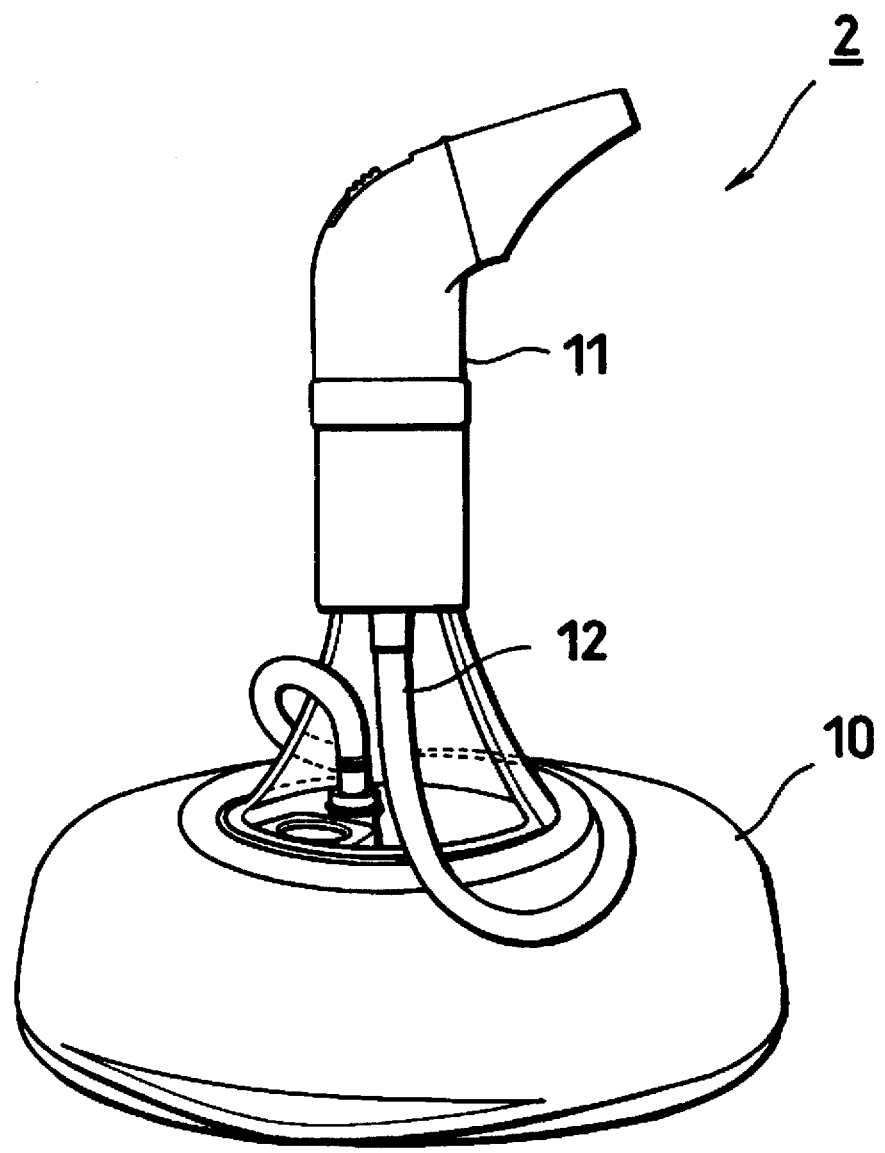
FIG. 3 is a perspective view of a portion of a portable unit of the system shown in FIG. 1.

The portable unit 2 has a sub-tank unit 10 which may also store a volume of the clean high-pressure air and reduce the pressure of the air to the level appropriate for atomization of inhalation medicine, and an atomizer 11 for generating mist of atomized medicine, as shown in FIG. 3.

The sub-tank unit 10 and the atomizer 11 are detachably connected with each other by a detachable air tube 12, as shown in FIG. 3.

Figure 4:
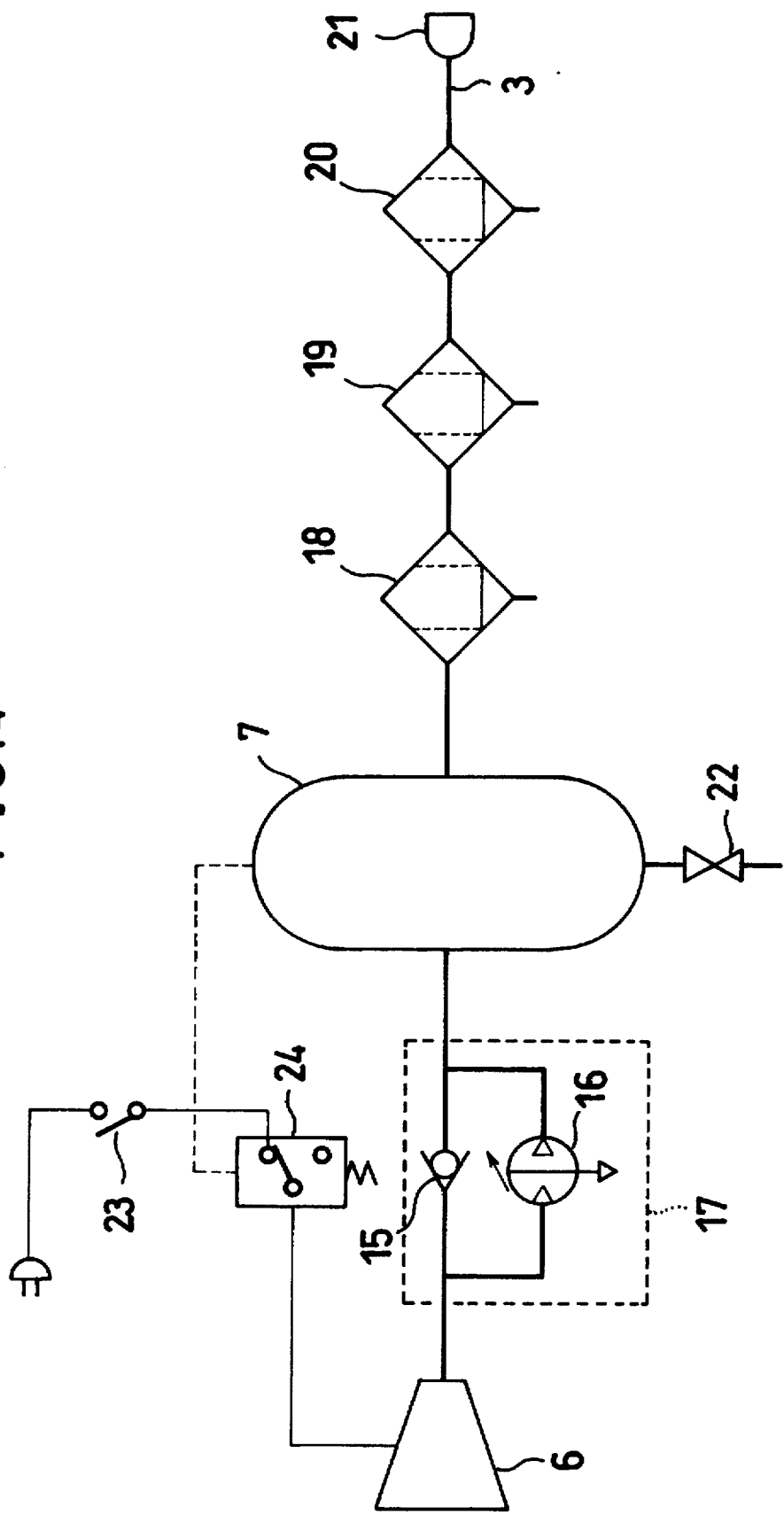
FIG. 4 is a diagrammatic representation of the structure of the main unit shown in FIG. 1.

Referring to FIG. 4, there is shown a functional structure of the main unit 1, in which the high-pressure air generated by the compressor 6 is passed through a pressure accumulator 17 into the main tank 7 with an increased pressure. The pressure accumulator 17 consists of a check valve 15 and a booster valve 16 for increasing the pressure of the air received.

The air stored in the main tank 7 is further passed to the air tube 3 via a sequence of a dust filter 18 for filtering dust in the air, an oil mist separator 19 for removing liquid particles in the air, and an odor filter 20 for eliminating odors in the air. Provided at the outlet of the air tube 3 is an air chuck 21 for stopping the clean high-pressure air. The main tank 7 is normally closed by the air chuck 21 when the atomizer is not in use, thereby maintaining a predetermined pressure therein.

The main tank 7 is provided with a drain valve 22 for draining water accumulated in the main tank 7. The compressor 6 is supplied with an AC voltage for actuating the compressor 6 through a power switch 23 and a pressure switch 24. The pressure switch 24 is designed to open when the pressure in the main tank 7 exceeds a predetermined level, for example 8 atms so that the compressor 6 is to be stopped, and close when the pressure in the main tank 7 drops below the predetermined level, thereby maintaining the pressure in the tank 7 at or near the predetermined level.

Figure 5A:
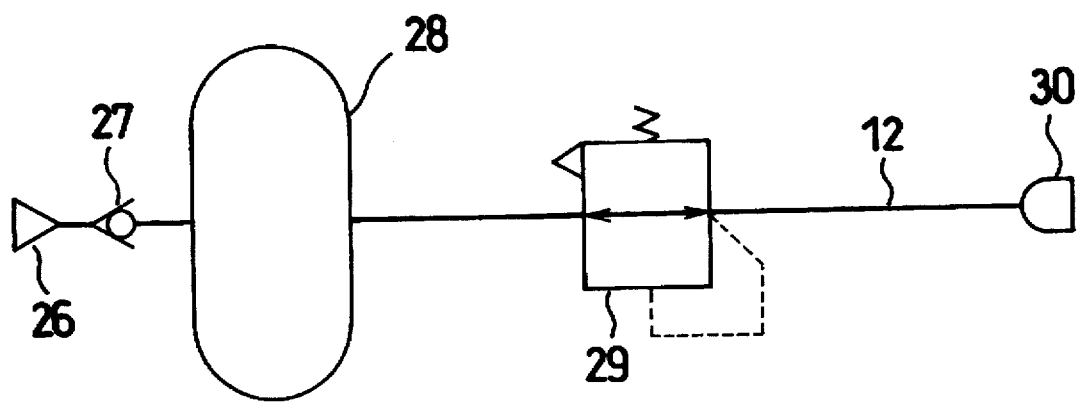
FIGS. 5A and 5B is a diagrammatic representation of the structure of the portable unit shown in FIG. 1.

Referring to FIG. 5A, there is shown a functional structure of the sub-tank unit 10 of the portable unit 2. As the air chuck 21 of the air tube 3 is connected to a sealing valve 26 of the portable unit 2, the air chuck 21 is opened to cause the clean high-pressure air to be injected into the portable unit 2.

The clean high-pressure air that has passed through the sealing valve 26 passes through a check valve 27 and into a sub-tank 28, which air is then decompressed to a pressure as low as, for example 0.5 atms, by a regulator 29. The decompressed air is released to the air tube 12. Provided at the tip of the air tube 12 is another air chuck 30 for stopping the air when the atomizer system is not in use. The air chuck 30 may be mounted on the regulator 29 and connected directly with the regulator 29 without using the air tube 12.

Figure 5B:
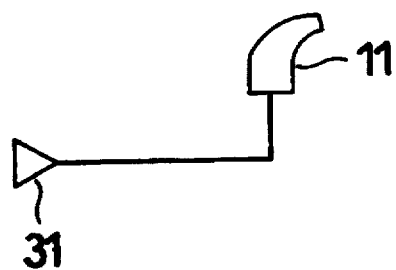

As shown in FIG. 5B, the atomizer 11 of the portable unit 2 is provided with a sealing valve 31 for removably connecting therewith the air chuck 30. Thus, when the air chuck 30 of the air tube 12 of the sub-tank unit 10 is mounted on the sealing valve 31 of the atomizer 11, the air chuck 30 is opened, thereby permitting the clean low-pressure air to flow into the atomizer 11.

Figure 6A:
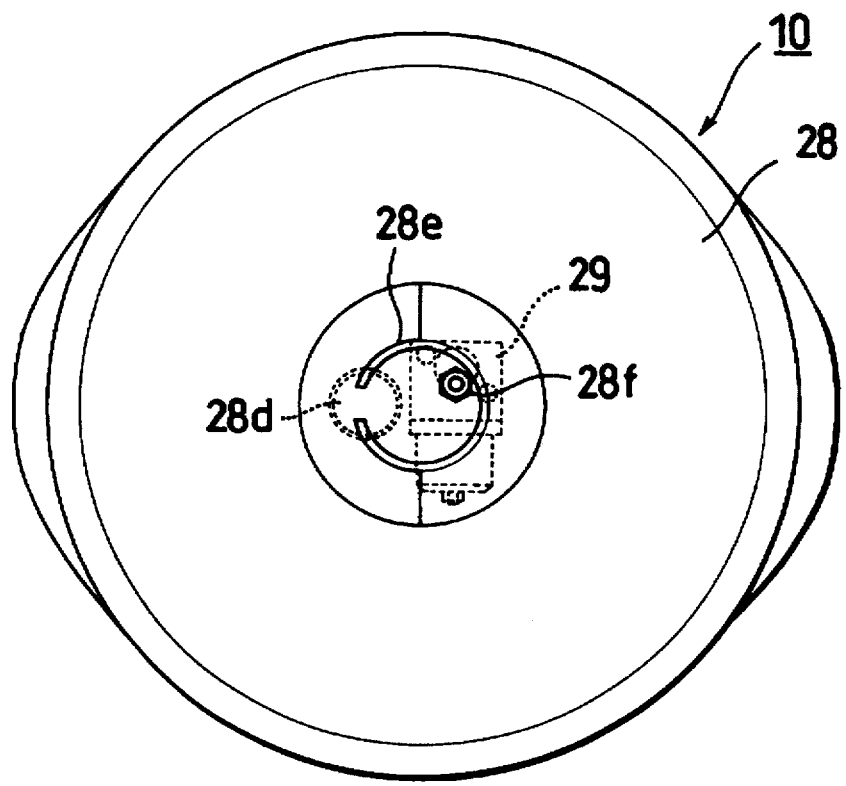
FIGS. 6A and 6B are a plan view and a side cross sectional view, respectively, of the portable unit shown in FIG. 5.
Figure 6B:
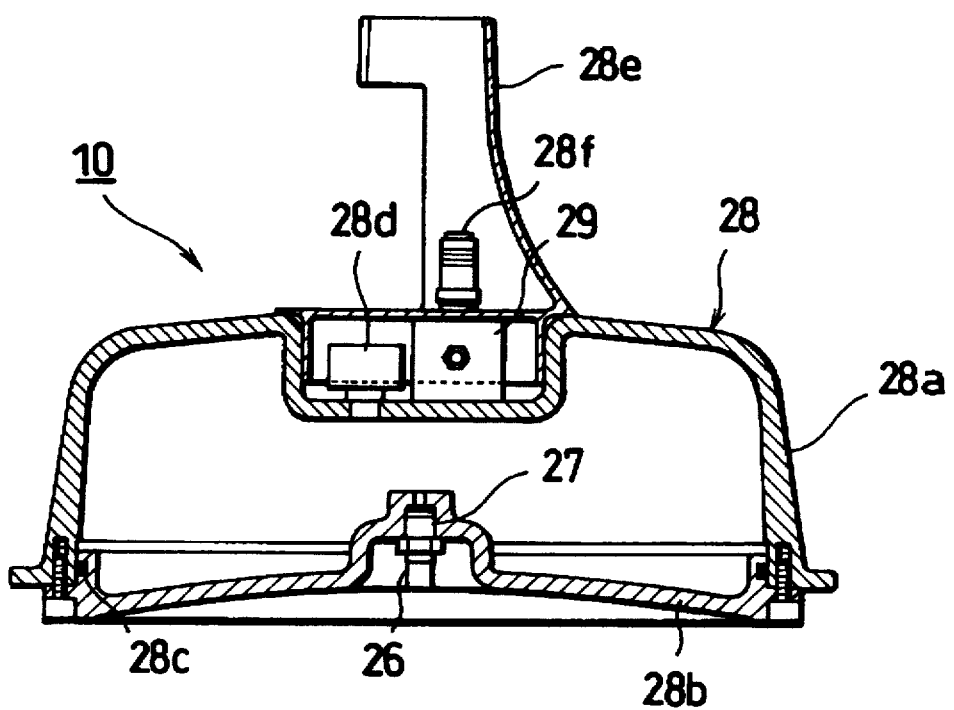

Referring to FIGS. 6A and 6B, the sub-tank 28 is shown to be a generally enclosed short cylinder having a shallow cylindrical central recess on the top thereof. The sub-tank 28 may be disassembled into an upper unit 28a and a bottom unit 28b. Inserted between the upper unit 28a and the bottom unit 28b is an O-ring 28c for enhancing sealability of the two units. A pressure gauge 28d is mounted on the upper unit 28a for indicating the pressure of the air in the sub-tank 28. A support member 28e is provided for the atomizer 11. A valve 28f is provided for controlling the flow of air through the air tube 12.

Since the sub-tank 28 is configured in the form of a generally short cylinder, the portable unit 2 may maintain its stability when placed on a flat level floor, thereby minimizing a risk of overturning of the portable unit 2 and of spilling the medicine out of the unit if a patient accidentally pushes it.

Since the sub-tank 28 is separable into the upper unit 28a and the bottom unit 28b, it is easy to clean the inside of the sub-tank 28, keeping it clean at all time.

The regulator 29 consists of a main unit 29a for reducing the pressure of the air received therein to a low level, and an upper unit 29b for setting the low pressure level, as shown in FIG. 7.

The main unit 29a receives clean pressurized air in a high pressure chamber 29c through a connection port 29d. The high pressure chamber 29c is fluid-dynamically connected with a low-pressure chamber 29e through a communication bore 29f. Provided at an intermediate section of the communication bore 29f is an outlet port 29g for allowing the low-pressure air to be taken out.

The upper unit 29b has a chamber 29h adjacent a low-pressure chamber 29e. The two chambers are partitioned from each other by a diaphragm 29i.

Mounted inside the chamber 29h is a pressure regulation spring 29j for pressing the diaphragm 29i downward. The length of the spring 29i may be adjusted by a pressure regulation screw 29k.

In order to support the diaphragm from below against the force of the spring 29j, there is provided in the communication bore 29f of the main unit 29a a stem 29m. The stem 29m is further supported by a ball valve 29n and a valve spring 29p which is in turn supported on the bottom of the high pressure chamber 29c. Thus, the force of the valve spring 29p acts on the stem 29m via the ball valve 29n, thereby pushing the diaphragm upward.

With this arrangement, the force of the pressure regulation spring 29j overbalances the force of the valve spring 29p acting on the diaphragm 29i prior to the injection of the high-pressure air into the high-pressure chamber 29c, so that the ball valve 29n is pushed down to a lower position as indicated by a solid line, thereby keeping the communication bore 29f communicating with the low-pressure chamber 29e.

As the clean high-pressure air is injected into the high-pressure chamber 29c, the high-pressure air passes into the low-pressure chamber 29e through the communication bore 29f, thereby raising the pressure in the low-pressure chamber 29e.

The pressure in the low-pressure chamber 29e will be raised until the resultant force of the valve spring 29p plus the force due to this pressure acting on the diaphragm 29i exceeds the force of the spring 29j so that the diaphragm 29i and hence the ball valve 29n are pushed up to close the lower end (high pressure end) of the communication bore 29f. This will stop the flow of the clean high-pressure air from the high pressure chamber 29c into the low-pressure chamber 29e.

When the high-pressure air flows into the low-pressure chamber 29*e*, a part of the air is ejected out of the outlet port 29*g* of the communication bore 29*f*. After the lower end of the communication bore 29*f* is closed by the ball valve 29*n*, the air trapped in the low-pressure chamber 29*e* continues to flow out of the communication bore 29*f* through the outlet port 29*g*.

Then the pressure in the low-pressure chamber 29*e* gradually decreases, since no air is supplied from the high-pressure chamber 29*c* to the low-pressure chamber 29*e* under this condition. This continues until the force acting on the diaphragm 29*i* due to the pressure in the low-pressure chamber 29*e* plus the force of the valve spring 29*p* is overbalanced by the force of pressure regulation spring 29*j*, when the diaphragm 29*i* is pushed down to restore its original position and open again the lower end of the communication bore 29*f*.

Consequently, the clean high-pressure air is replenished from the high-pressure chamber 29*c* into the low-pressure chamber 29*e*, repeating in sequence the above mentioned upward and downward motions of the diaphragm caused by imbalances of the two forces acting on the diaphragm 29*i* due to the spring 29*j* and the varying pressure in the low-pressure chamber 29*e*, which results in intermittent open/close operations of lower end of the communication bore 29*f* by the ball valve 29*n*.

In this manner, the high-pressure air supplied from the connection port 29*d* is transformed into clean low-pressure air, which is stored in the low-pressure chamber 29*e* and released from the outlet port 29*g*. This pressure is regulated by the pressure regulation spring 20*j*.

Figure 8:
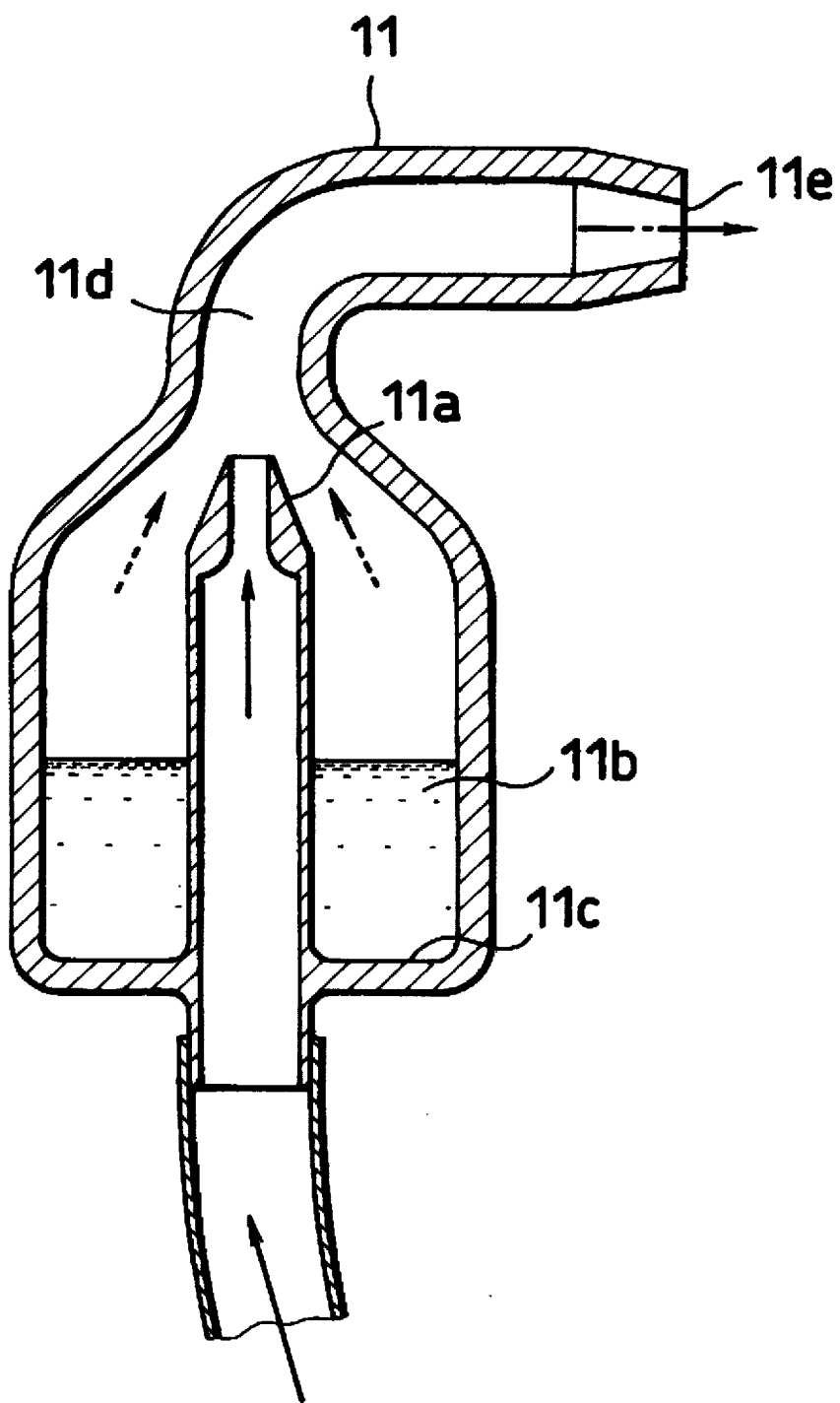
FIG. 8 is a cross sectional view of an atomizer unit of the portable unit.

The atomizer 11 is provided with a nozzle 11*a* as shown in FIG. 8. A reservoir 11*c* surrounding the nozzle 11*a* is provided for storing therein inhalation medicine 11*b*. The upper end of the reservoir 11*c* is configured to converge so that it provides a narrow passage for the medicine over the nozzle 11*a*, and a mixing section 11*d* formed between the narrow passage and an ejection tip 11*e* of the atomizer unit.

When the low-pressure air is injected into the atomizer 11, the air is ejected from the nozzle 11*a* as a high speed jet of air. The high speed jet draws in ambient air into the mixing section 11*d*, thereby creating a negative pressure in the upper region of the reservoir 11*c*, so that evaporation of the medicine into the mixing section 11*d* is enhanced.

In the mixing section 11*d*, the evaporated medicine 11*b* is mixed with the air jet coming out of the nozzle 11*a*, and then ejected from the ejection tip 11*e*. In this manner a jet containing the medicine 11*d* is ejected out of the ejection tip 11*e*.

In the utilization of this system in inhalation purposes, the main unit 1 may be installed anywhere, such as a nurse station, convenient in operating the compressor, so that the high-pressure air needed for the atomizer unit 2 may be prepared there. First, the switch 23 is closed to activate the pressure switch 24, which, in turn, energizes the compressor 6 to generate high-pressure air.

The high-pressure air thus compressed is further compressed by the action of the pressure accumulator 17 and builds up in the main tank 7. The high-pressure air in the tank 7 is cleaned when it is passed through a dust filter 18, an oil mist separator 19, and an odor filter 20. The clean air is led to the air chuck 21 via the air tube 3. Since the air chuck 21 has been closed during this operation, the pressure of the air gradually increases until the pressure reaches a predetermined level, when the pressure switch 24 is opened, thereby stopping the compressor 6.

In this manner, when the power switch 23 of the main unit 1 is closed to actuate the compressor 6, the main tank 7 is charged with high-pressure air until the pressure in the tank 7 reaches the preset value. One may confirm the pressure in the main tank 7 by reading the indication of the pressure gauge (FIG. 2) mounted on the main tank 7. It will be noted that when a part of the high-pressure air is given to the portable unit 2 and the pressure in the main tank 7 lowers below a preset level, the pressure switch 29 is again closed to actuate the compressor, to bring the pressure back to a desired level in the tank 7. Thus, the main tank 7 is always maintained at a desired pressure.

In order to supply the portable unit 2 with the high-pressure air, the air chuck 21 of the air tube 3 belonging to the main unit 1 is mounted on the sealing valve 26 of the portable unit 2. It should be noted that the air chuck 30 of the air tube 12 belonging to the portable unit 2 is not yet connected with the sealing valve 31 of the atomizer 11. The support member 28*e* of the atomizer 11 may be dismounted from the sub-tank 28 and kept at a place (e.g. bedside) convenient for the patient. Therefore, for patient's convenience, only the sub-tank unit 10 of the portable unit 2 needs to be transported between the nurse station and the patient's room.

Connecting the air chuck 21 with the valve 26 causes the air chuck 21 to be opened, allowing the clean high-pressure air to flow from the main tank 7 into the sub-tank 28 of the portable unit 2 via the air tube 3, the air chuck 21, the sealing valve 26, and the check valve 27. It will be recalled that the air is cleaned as it passes to the air chuck 21 through the dust filter 18, the oil mist separator 19, and the odor filter 20. The clean air is now stored in the sub-tank 28 and has reached the air chuck 30. If the air chuck 30 is connected with the sealing valve 31 of the atomizer 11, the clean high-pressure air loaded in the sub-tank 28 will be transformed into a low-pressure air having a predetermined pressure by the regulator 29 and passed to the atomizer 11 through the air tube 12 and the air chuck 30.

However, since the air chuck 30 is not connected with the sealing valve 31 in this situation, the air chuck 30 stops the clean (low-pressure) air, and thus the pressure in the sub-tank 28 gradually rises to substantially the same level as in the main tank 7. The user of the system may confirm the pressure in the sub-tank 28 from the indicator 28*d*.

In the manner as described above, by loading clean high-pressure air in the sub-tank 28 of the portable unit 2 and bringing the portable unit 2 to the site where it is needed, the treatment may be easily conducted. The support member 28*e* is mounted on the sub-tank 28 at the site, and the atomizer 11 is set up on the support member 28*e*. Then an inhalant 11*b* is injected in the atomizer 11 from the ejection tip 11*e*. Following this, the air chuck 30 of the air tube 12 is connected with the sealing valve 31. The mounting the air chuck 30 with the sealing valve 31 causes the air chuck 30 to open, so that the clean high-pressure air stored in the sub-tank 28 is now injected into the atomizer 11 via the air tube 12, the air chuck 30 and the sealing valve 31 after the air is transformed to low-pressure air by the regulator 29. The low-pressure air reaching the atomizer 11 will atomize the medicine 11*b* and eject a jet of the atomized medicine from the ejection tip of the atomizer 11 for the patient, as previously described.

It should be appreciated that since this portable unit 2 has no compressor or any other mechanical components operated by a motor, treatment may be performed very calmly without a fear of bothering other patients in the room if the unit is used at the bed side of the patient.

It should be also appreciated that the volume of the sub-tank 28 may be small, since only a required amount of clean pressurized air is stored in the sub-tank 28 of the portable unit 2 and the pressurized air is transformed into low-pressure air by the regulator 29 while it is used. As an example, assuming that the pressure of the air in the sub-tank 8 is 8 atms, the regulator 29 reduces this pressure to 0.5 atms, and a running period is 5 minutes, a required volume of the tank 28 may be as small as 2 liters.

Thus, it would be understood that the invention provides a compact and calm inhaler, which may be used anytime and anywhere without a fear of causing a nuisance to other people.

Advantageously, since the atomizer 11 is removable from the portable unit 2, it may be replaced with the same type of atomizer 11. This not only permits simple replacement of the atomizer 11 for convenience, but also contributes reduction of manufacturing cost of atomizer units 11 through mass production thereof.

Referring to FIGS. 9 through 19, alternative systems of the invention will be described below. In these figures like or corresponding elements carry like reference numbers as in FIGS. 1 through 8.

An alternative example shown below is suitable as an inhaler for use in a medical clinic or a hospital where a movable system must be used in treating patients having respiratory illness.

Figure 9:
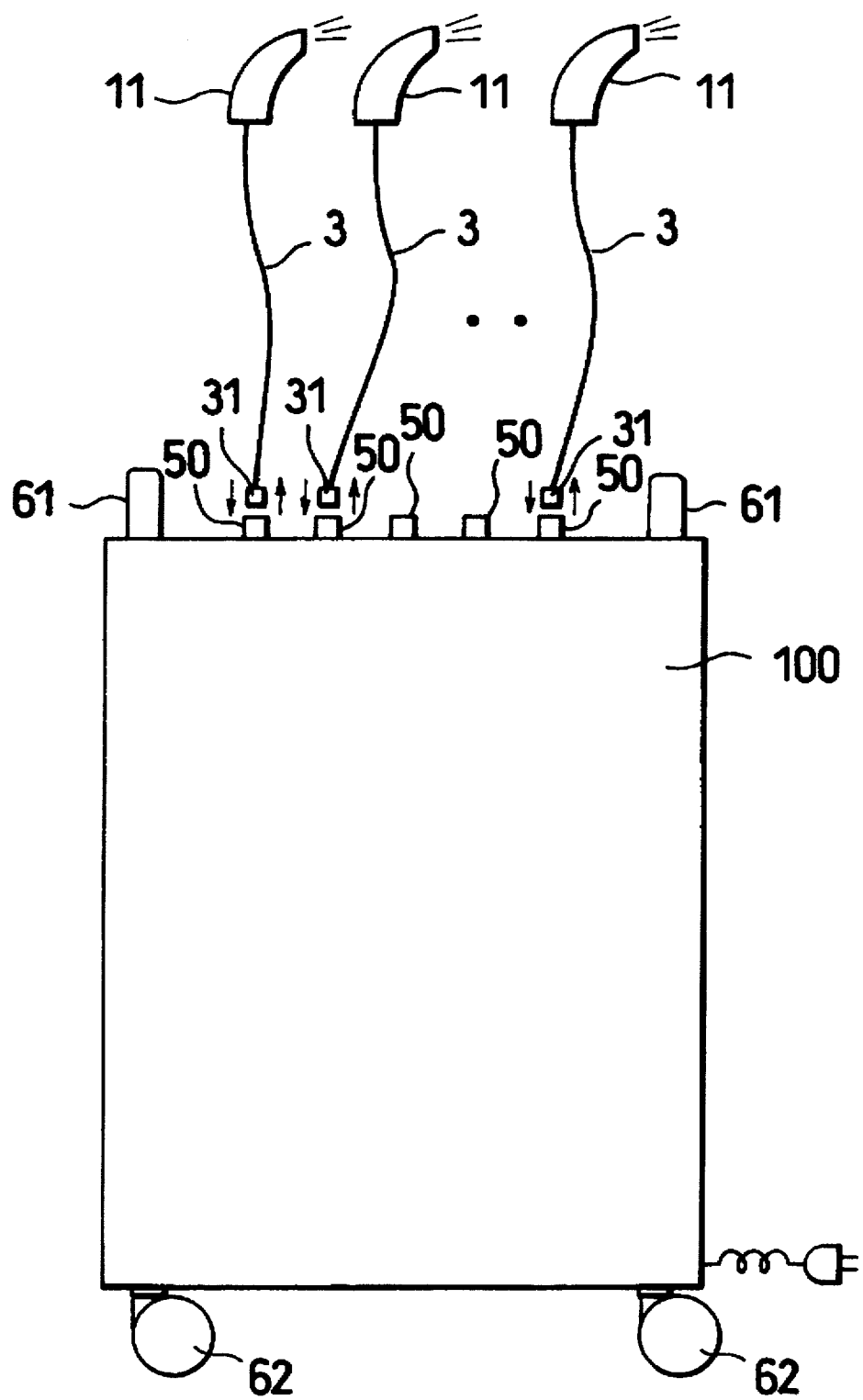
FIG. 9 is a schematic view of a second atomizer system according to the invention.

FIG. 9 shows an atomizer system which comprises a movable main unit 1 for generating and storing clean high-pressure air, and a multiplicity of atomizers 11 connectable with a corresponding number of clean low pressure air outlets 50.

The clean low-pressure air generated in the main unit 1 is sent to the atomizer 11 through respective air tubes 3 which are removably connected with arbitrary ones of the air outlets 50.

Thus, as seen in FIG. 9, patients as many as the number of the air outlets may be treated simultaneously by connecting the same number of air tubes 3 with the air outlets 50.

The main unit 1 has at the bottom thereof casters 62, and at the top thereof a pair of hand rails 61, so that it may be easily moved by simply pulling or pushing the hand rails 61.

Figure 10:
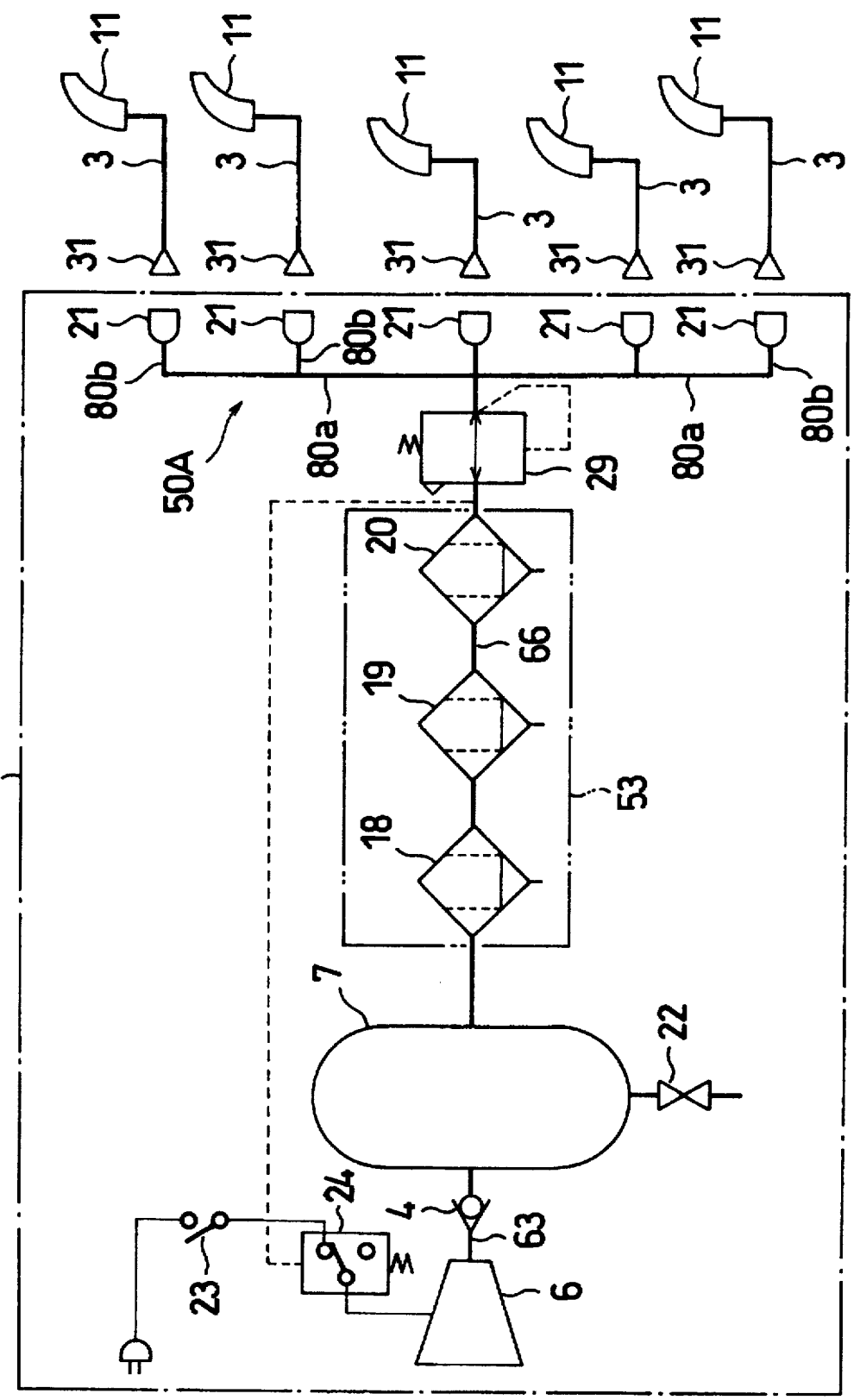
FIG. 10 is a diagram representation of the atomizer system shown in FIG. 9.

Referring to FIG. 10, there is shown a further example of the atomizer system according to the invention, in which a main unit 1 as indicated by a dotted line includes a compressor 6 for generating high-pressure air, a pressure accumulation tank 7 (hereinafter referred to as tank) for storing the high-pressure air supplied from the compressor 6 via a check valve 4 provided in a tube 63, a filter unit 53 placed in a communication tube 66 and accommodating three kinds of filters for removing different contaminants to thereby clean the high-pressure air, a regulator 29 for reducing the pressure of the cleaned air received from the tank 7 to a predetermined level suitable for atomization of an inhalant, and an air outlet unit 50A having a set of air outlets 50 (FIG. 9) for supplying clean low-pressure air from the regulator 29.

The filter unit 53 is provided to remove various contaminants contained in the high-pressure air subsequent to storage in the tank 7 and before delivery to the regulator 29 where the air is decompressed prior to further delivery to the air outlets 50. Thus, the filter unit 53 is installed downstream of the tank 7 and upstream of the regulator 29. The filter unit 53 comprises a dust filter 18 for removing dust in the air, an oil mist separator filter 19 for removing liquid particles, and an odor filter 20 for removing odors in the order mentioned.

These filters each have indicator sections which change their colors when they are choked with contaminants as a result of long term use, indicating that they need to be replaced.

In these cases the filters may be easily replaced because the filters are removably mounted, as described in detail subsequently.

Referring again to FIG. 10, the air pressurized by the compressor 6, and stored once in the tank 7 is sent to the regulator 29 through the tube 63 after it is cleaned by the filters 18, 19, and 20, as described above, and is decompressed in the regulator to a level, for example 0.6 atms. The clean decompressed air or low-pressure air is delivered to the air outlet unit 50A and reaches each end of the air outlets 50.

Provided at the exit end of each air outlet is an air chuck 21 for blocking the clean low-pressure air when the system is not in use. The air in the tank 7 is then maintained at a high static pressure when the air chuck 21 is closed.

The compressor 6 is supplied with an AC power through a power switch 23 and activated by a pressure switch 24. The pressure switch 24 is operable in response to the pressure of the air coming out of the filter unit 53 in such a way that the compressor 6 is turned off when the pressure in the tank 7 exceeds a predetermined level of, for example 8 atms, and is turned on when the pressure in the tank 7 drops below the predetermined level, thereby maintaining the pressure of the air in the tank 7 at substantially the same level.

Figure 11:
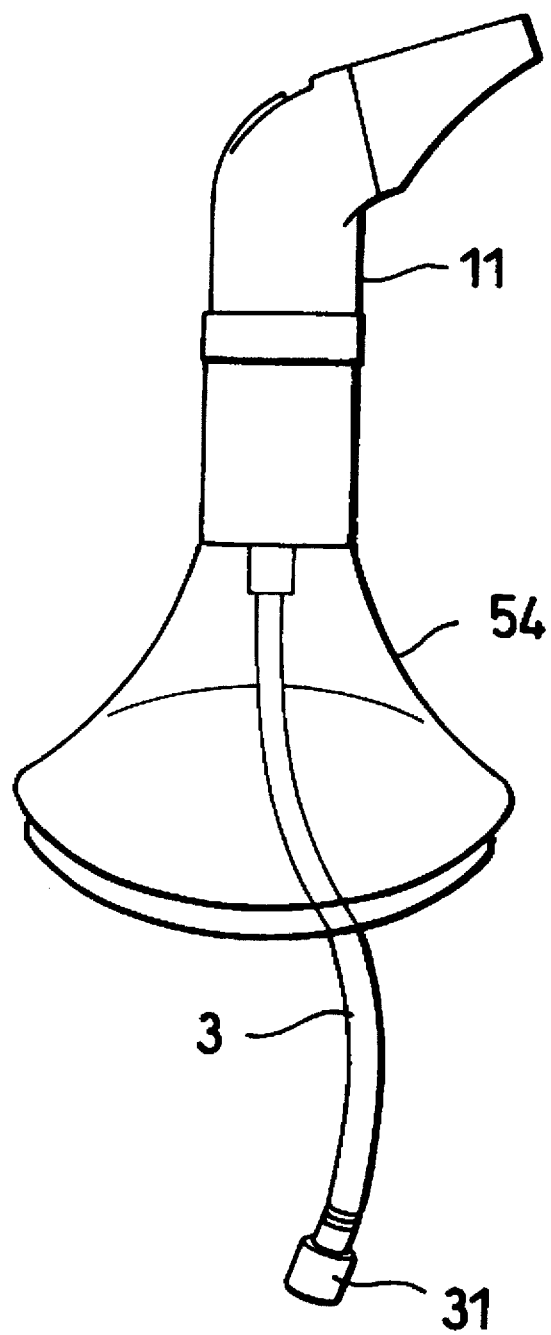
FIG. 11 is a perspective view of an inhalator using the atomizer unit of the invention.

An atomizer 11 has a compact configuration as shown in FIG. 11 for atomizing an inhalant by the clean low-pressure air from the main unit 1. When the atomizer is not in use, it may be secured on a stand 54. The atomizer 11 has an air tube 3 extending from the bottom of the atomizer 11 and having at one end thereof a sealing valve 31 which may be removably connected with any one of the air chucks 21 of the respective air outlets 50. When the sealing valve 31 of the atomizer 11 is connected with the air chuck 21, the air chuck 21 is opened to permit the clean low-pressure air to flow from the air outlets 50 to the atomizer 11.

A drain valve 22, similar to the one shown in FIG. 10, is connected to the tank 7 for draining water accumulated in the tank 7. The drain valve 22 may be advantageously utilized not only for draining the water but also for removing dust and air in the tank 7. Thus, it may be used as an extra air outlet other than the air outlets 50 for some pneumatic operations.

Figure 12A:
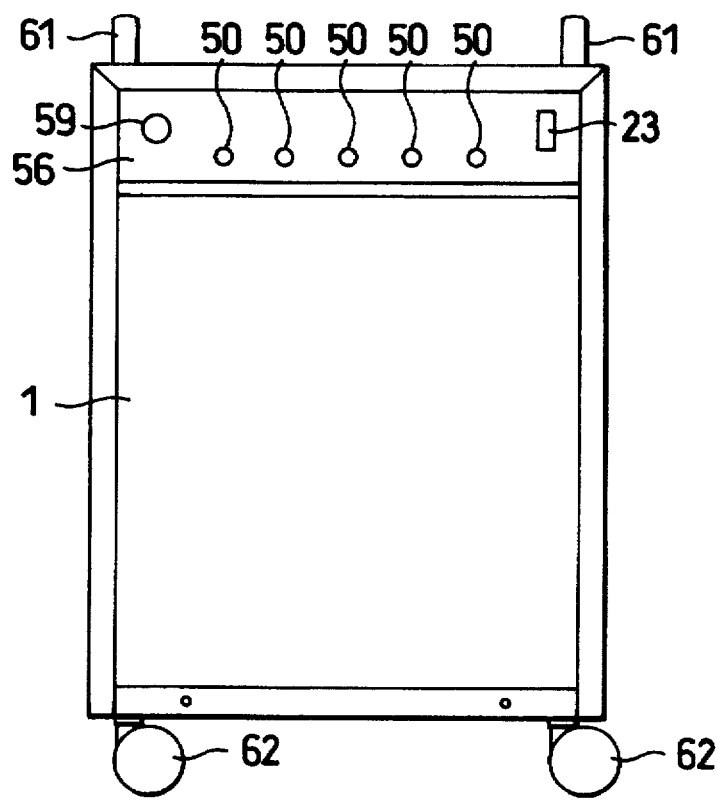
FIGS. 12A, 12B, and 12C are a front view, a side view, and a plan view, respectively, of the atomizer system shown in FIG. 9.
Figure 12B:
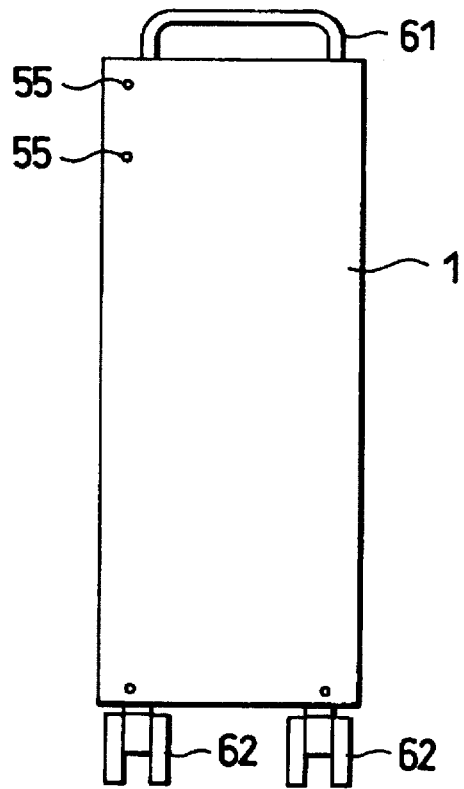
Figure 12C:
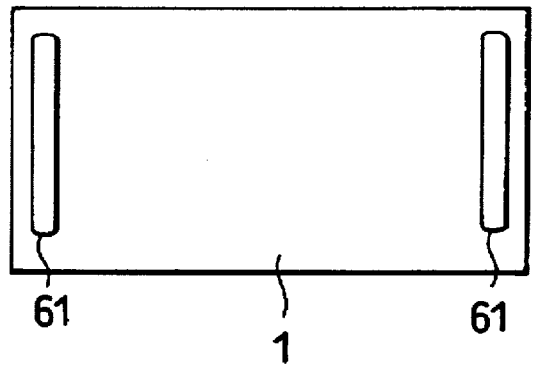
Figure 13A:
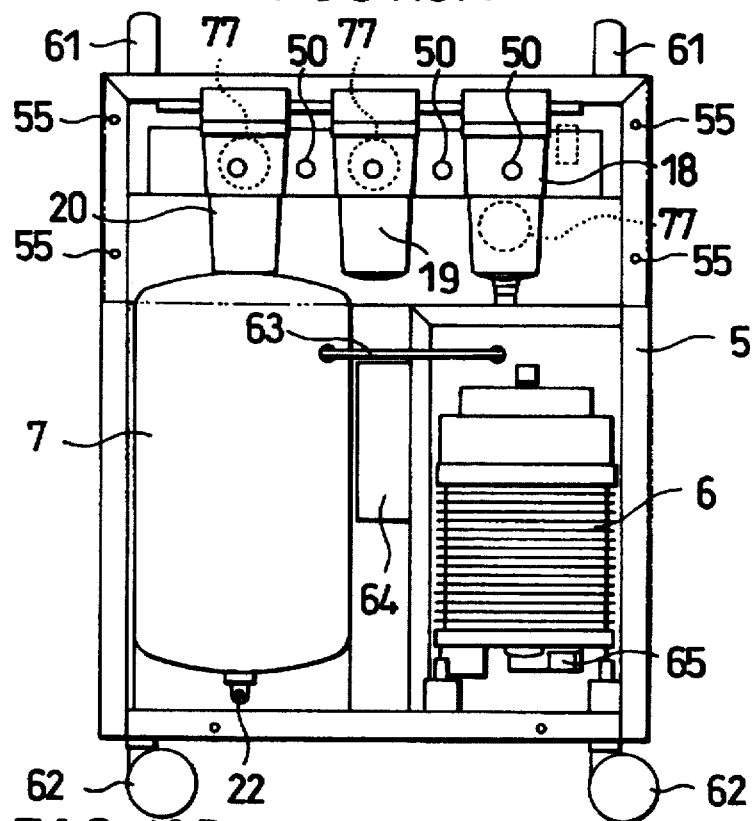
FIGS. 13A, 13B, and 13C show the arrangement of the main body of the atomizer system as viewed from the front, the side and the top of the system, respectively.

Referring now to FIGS. 12 and 13, details of the main unit 1 of a third example will be described. As shown in FIG. 12, a thin and rather tall rectangular housing 5 of a main unit I has an air outlet unit 50A having five air outlets 50 for releasing low-pressure air on a control panel 56 located at an upper front corner of the main unit 1. The air outlets are horizontally spaced apart at a regular interval. These air outlets 50 are fixedly mounted in respective bores 57 made in the control panel 56, as shown in FIG. 14. The panel 56 may be removed from the main unit by unthreading the screws 55 secured on the opposite sides of the main unit as shown in FIG. 12B. Also mounted on the control panel 56 is a power switch 23 for actuating a compressor 6 and an observation window 59 for monitoring a pressure gauge 69 indicating the pressure of the air generated by the atomizer system.

A pair of hand rails 61 is provided on the top of the main unit 1 so that an operator may lift or move the main unit 1.

The compressor 6 is installed at a right lower corner of the housing 5 as shown in FIG. 13, and a tank 7 at a left lower corner of the housing 5. The tank 7 and the compressor 6 are connected with a tube 63.

The compressor 6 is firmly secured on the bottom of the housing 5 by screws, with vibration absorbing bushes placed between them. The compressor 6 may be an oilless scroll compressor. When a scroll compressor is used, a cooling fan 64 is provided in a space between the compressor and the tank 7 for cooling the compressor, since the oilless compressor generates heat during its operation. A relay 65 is also provided for turning on the compressor.

We will now describe in detail the filter unit 53 for cleaning the air before the air is sent to the regulator 29 from the tank 7.

Figure 13B:
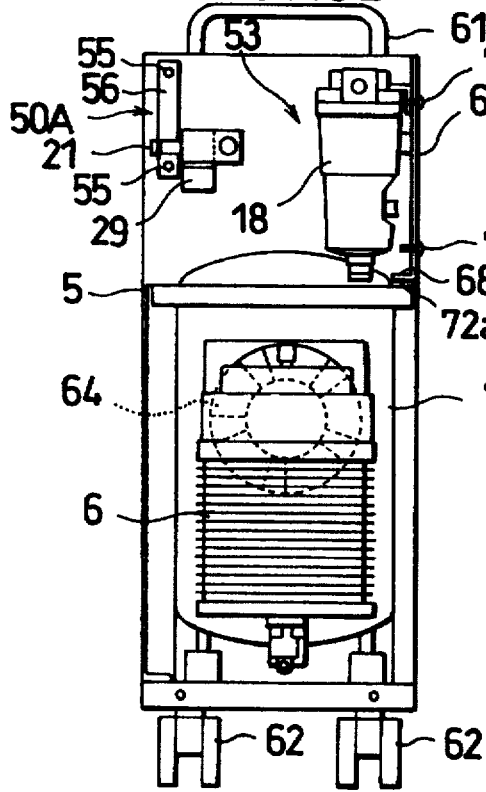
Figure 13C:
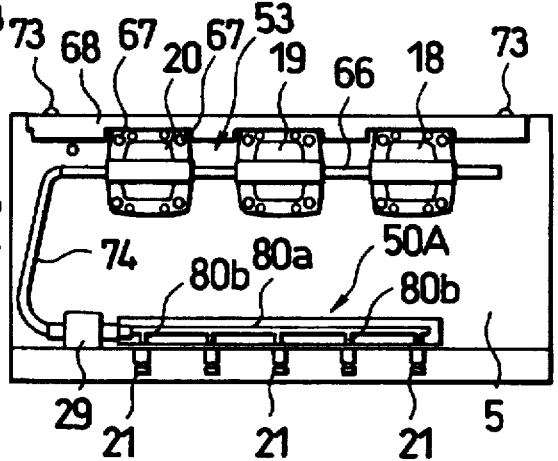
Figure 14:
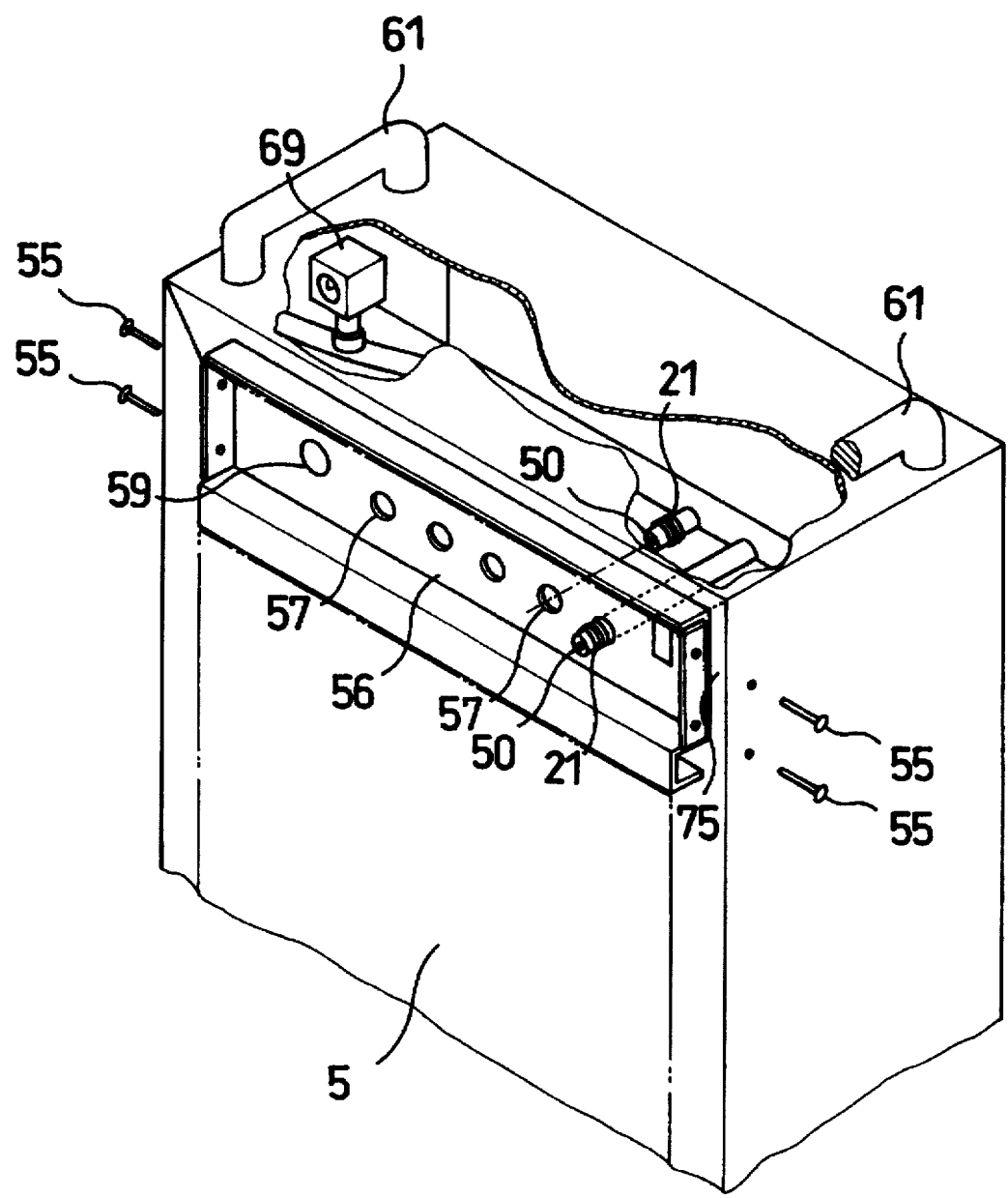
FIG. 14 a perspective view of the main unit, partially cut away for illustration of air outlets to be connected with the main unit shown in FIG. 9.
Figure 15:
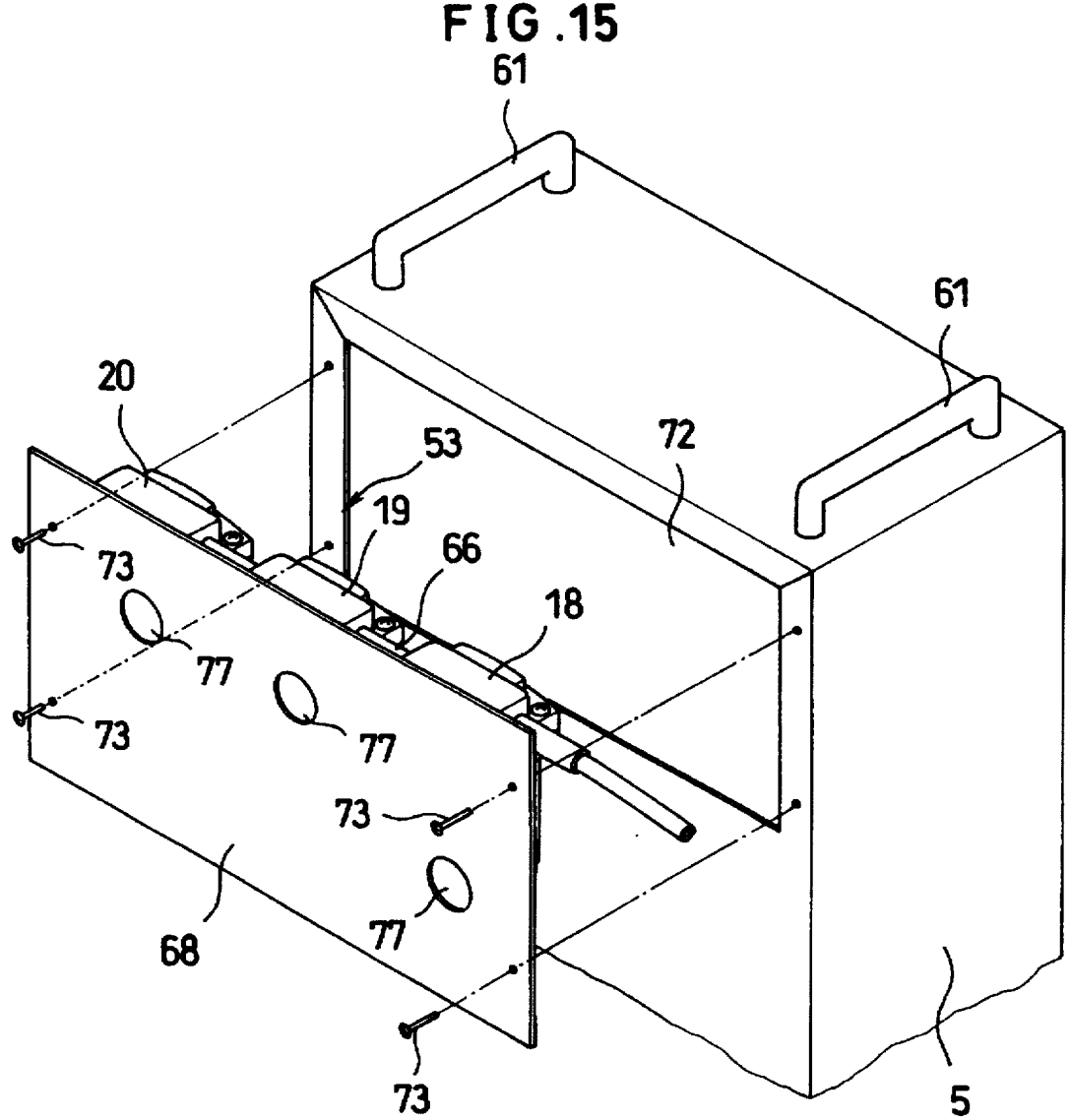
FIG. 15 is a perspective view of the main unit, partially exploded for illustration of air filter units to be connected with the main unit shown in FIGS. 9.
Figure 16:
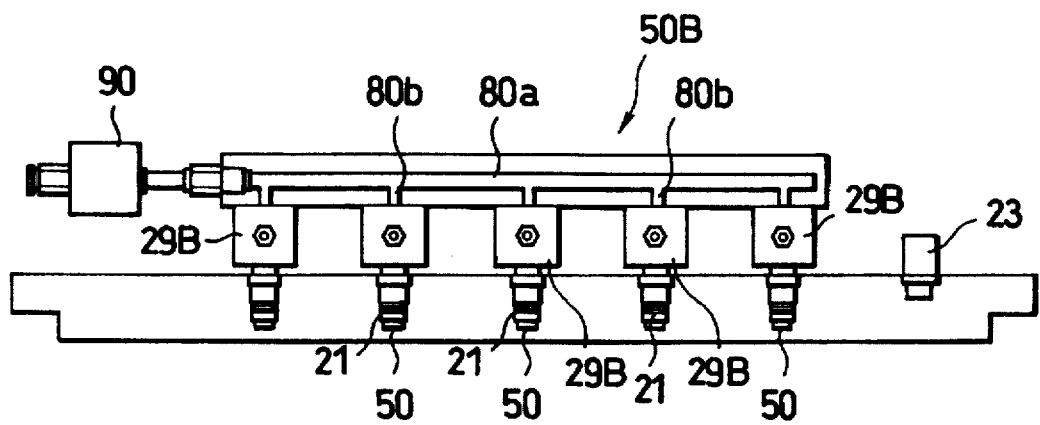
FIG. 16 is a plan view of a set of air outlets provided in the main unit of the system shown in FIG. 9.
Figure 17:
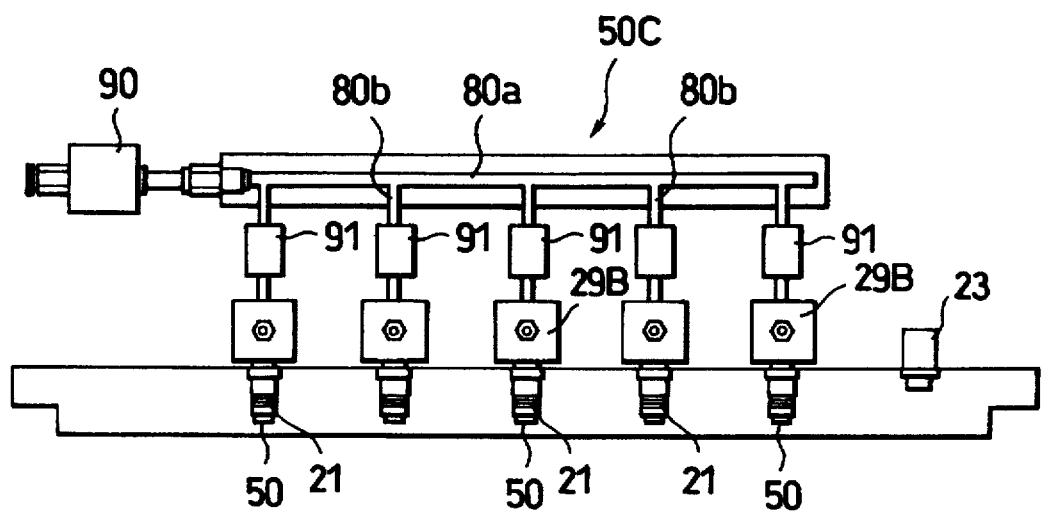
FIG. 17 is a plan view of a further set of air outlets provided in the main unit of the system shown in FIG. 9.
Figure 18:
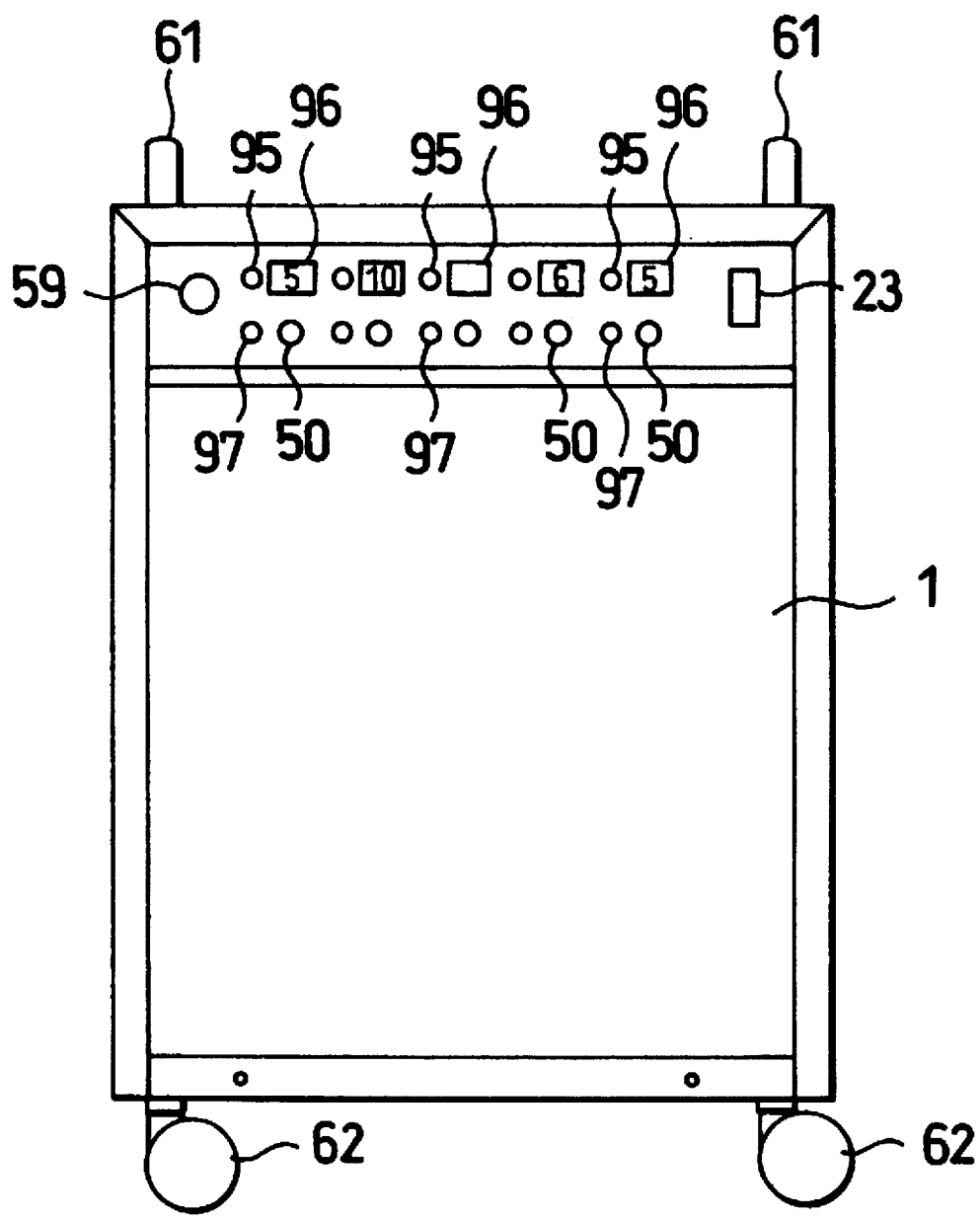
FIG. 18 is a front view of the main unit of the system having the air outlets shown in FIG. 17.
Figure 19:
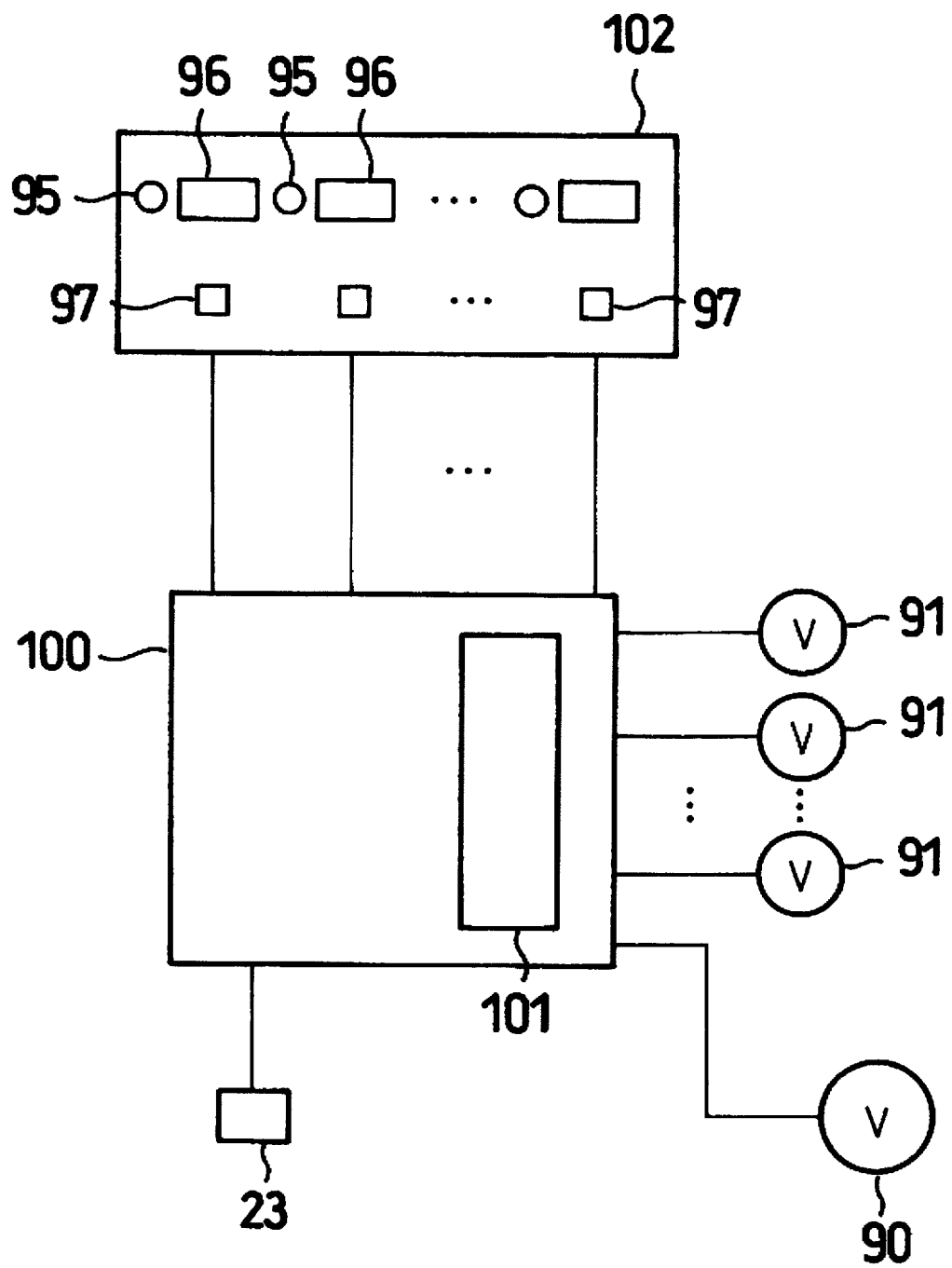
FIG. 19 is a diagram representation of a timer unit for controlling the timing of passage of the air through the air outlets shown in FIG. 17.

As shown in FIG. 13, a filter unit 53 is mounted on an upper corner of a back panel of the housing 5. The filter unit 53 includes a dust filter 18, an oil mist separator 19, and an odor filter 20 arranged and integrated together in series in the order mentioned. A panel (filter mount panel) 68 is used to mount these filters in integration. The lower end of the filter mount panel 68 is folded inwardly so as to form a flange 68a (FIG. 13B). The filter unit 53 may be secured on the back side of the panel 68 by three sets of screws 67 (FIG. 13C).

The back panel of the housing 5 has an opening 72 (FIG. 15) whose dimensions correspond to the dimensions of the filter mount panel 68. At the lower end of the opening 72 is a flange 72a (FIG. 13B) for supporting thereon the flange 68a when the filter mount panel 68 is placed in position over the opening 72. The filter mount panel 68 may be mounted on the housing 5 by first placing it on the back panel with its flange 68a in alignment with the flange 72a, and then securing the filter mount panel 68 by four screws 73 threaded into right and left threaded bores. The panel 68, and hence the filter unit 53, may be easily removed by removing these screws.

In order to observe color changes that take place in the indicator sections of the three filters 18, 19, and 20, an observation window 77 is provided in a corresponding position of the filter mount panel 68.

When the colors of the filters have changed as observed through the observation window, the filter mount panel 68 carrying thereon the filter unit 53 is removed from the main unit 1 by removing the screws 73, and the filters 18, 19, and 20 are replaced with new ones by removing the screws 67. The filter mount panel 68 now having the new filters is mounted again over the opening 72. This completes the replacement of the filter unit 53.

It would be appreciated that in this design the filter unit 53 may be easily mounted and dismounted by simply mounting and dismounting filter mount panel 68, so that repair and replacement of the unit 53 may be carried out without difficulty.

The air outlet unit 50A having five air outlets 50 is mounted at an upper position in the housing 5 such that the filter unit is located right behind the air outlet unit 50A. The air outlet unit 50A includes a main tube 80a which is connected at one end thereof with a regulator 29 which is similar to the one mentioned previously and has at the other end five branching tubes 80b. The regulator 29 is connected with the filter unit 53 with a communication tube 74 (FIG. 13C). Air chucks 21 similar to those previously described in connection with FIGS. 4 and 10 are provided in the exit ends of the branching tubes 80b one for each branching tube.

It would be understood that the air outlet unit 50A may be manufactured as a separate unit, so that it may be conveniently mounted and dismounted on the control panel 56. Next, the control panel 56 itself is removably fitted in an opening 75 of the housing 5 and secured on the housing 5 by means of screws 55. Thus, assembly and disassembly of the air outlet unit 50A may be carried away in a simple manner for maintenance such as cleaning and repair thereof. The same is true for a regulator 29 for the adjustment of the pressure level of the air. The basic structure of the regulator 29 is the same as that of a corresponding element described in connection with FIGS. 7 and 8. The same is true for an atomizer 11.

In operation, when the switch 23 is closed, a pressure switch 24 is turned on to energize the compressor 6, which in turn starts generating high-pressure air.

The high-pressure air is stored in the tank 7, which is then passed to the regulator 29 via the dust filter 18, the oil mist separator 19, and the odor filter 20 in sequence so that the air is cleaned before it reaches the regulator 29. The high-pressure air thus cleaned and led to the regulator 29 is decompressed therein to a predetermined level. This decompressed clean air is distributed to the air chucks 21 through the respective branching tubes 80b of the main tube 80a. When the air chucks 21 are closed, the air builds up in the regulator 29 and the tank 7 as well, increasing the pressure in the tank 7 until the pressure reaches the preset level. As the pressure reaches the preset level, the pressure switch 24 is opened to thereby stop the operation of the compressor 6. The pressure in the tank 7 may be found by a pressure gauge 69 (FIG. 14) mounted on the tank 7, so that the patient using the system or the nurse attending the system may quickly find malfunction of the system if any and stop the operation for safety and for subsequent repair thereof.

As the atomizer 11 is connected with one of the air outlet 50 via the air tube 3 of the atomizer 11, the low-pressure air loaded in the tank 7 and the regulator 29 is released to the atomizer, so that the pressure decreases in the tank 7. When the pressures lowers to a preset level, the pressure switch 24 is again activated, restarting the compressor 6 to supply pressurized air to the tank 7.

In order to utilize the high-pressure air stored in the tank 7 with the atomizer 11, the sealing valve 31 provided at the entrance end of the atomizer 11 is mounted in one of the air chucks 21.

This causes the air chuck 21 of the air outlet 50, to which the air tube 3 is connected, to be opened, so that the high-pressure air is released from the tank 7, which is cleaned by the filters 18, 19, and 20 as described previously, and decompressed in the regulator 29. The air is finally ejected into the atomizer 11 via the air chuck 21, the sealing valve 31 and the air tube 12, thereby atomizing an inhalant 11b and ejecting it from the nozzle 11a of the atomizer 11 in the form of an jet containing the inhalant, which is inhaled by the patient. In this way the patient may be treated in his room without moving out of the room. The treatment is thus performed in a very convenient manner any time he needs it.

In a case where the atomizer system is installed in a treatment room for outpatients, a required number of atomizers 11 may be simultaneously connected to the air outlets 50 by mounting the air tubes 3 on the air chucks 21, allowing the individual atomizers 11 to be used by the same number of patients. This helps minimize work of the nurses and other attendants. It would be obvious that although five air outlets 50 are provided in the example shown herein, it is possible to set up an arbitrary number of air outlets 50.

It would be appreciated that, since the system is movable, it may be moved for use to any desired place, for example a place suitable to protect the privacy of the patients.

In the example shown herein having only one regulator 29 for providing low-pressure air to all of the five air outlets 50, it can happen that the air pressures drop low in those air outlets 50 remote from the regulator 29 due to resistive forces caused by the friction between the air and the wall of the tube 80a. Such pressure drop would result in uneven flow rates of the air from the air outlets 50. Furthermore, if an additional air outlet 50 closer to the regulator 29 is used while operating another at a remote outlet 50, the pressure in the remote air outlet can fluctuate, which causes instabilities in the atomization of the inhalation medicine in the atomizer 11 and resulting in instabilities in the treatments of the patients.

As an improvement to this, one may use an air outlet unit 50B as shown in FIG. 16, which permits more stable operation of the system for the reason discussed below. In this example, each of the branching tubes 80*a* of the air outlet unit 50B is provided with a regulator 29B. The air flow to the air outlet unit 50B may be controlled by an electromagnetic valve 90 which is actuated by the power switch 23, as shown in FIG. 16.

With these regulators provided one for each of the air outlets 50, it is possible to provide each of the branching tubes 50*b* with the low-pressure air having a prescribed pressure regulated by the corresponding regulator 29B.

In operation, upon closing the power switch 23, the electromagnetic valve 90 is opened, so that the air tubes 3 of individual atomizers 11 are fluid dynamically connected with respective air outlets 50. Under such conditions, the air outlets 50 are supplied from the respective regulators with low-pressure air having desired pressures suitable for the atomizers 11 connected.

If all of the five atomizers 11 are connected with the corresponding air outlets 50, they will receive low-pressure air from any of the air outlets 50 irrespective of their positions with respect to the regulator without any pressure drop or fluctuations as mentioned above. That is, the air outlets 50 will receive the air uniformly, so that all the patients may be treated in stable conditions with the atomizers 11.

In the preceding two examples, the air outlets 50 are adapted to open when the sealing valve 31 provided at the end of the air tube 3 of the atomizer 11 is connected with one of the air chucks 21. This design of the air outlets 50, however, has a little disadvantage in that at the moment the air outlet 50 is connected with the air tube it is instantly opened and begins to release the low-pressure air into the atomizer 11 and generate a jet of the medicine. If the atomizer 11 has not been properly set in the patient's mouth prior to the connection, the patient might be hit in the face by the sudden jet of the medicine, or fail to introduce the jet into his mouth. This means that the patient must be ready for the treatment before the air tube 3 is connected with the air outlet. To improve the system in this respect, each of the branching tubes 80*b* of the air outlet unit 50C may be provided with an electromagnetic valve 91 as shown in FIG. 17.

Each of the electromagnetic valves 91 is adapted to be opened for a predetermined period of time as scheduled by a timer. This allows automated ejection of a particular kind and quantity of medicine to each patient for a given period of time in accordance with the prescription to the patient, enabling efficient treatments of all the patients.

For this automated operation to be carried out, there is provided a set of timing switches 95, a set of time indicators 96, and a corresponding set of starter switches 97 (FIG. 19) associated with the air outlets 50, as shown in FIG. 18. Thus, a nurse may set a proper period of time for a patient by the timing switch 95 associated with the air outlet for the patient. The corresponding time indicator 96 indicates the period set by the timing switch 95 as well as the remaining period of time after the treatment is started. The electromagnetic valve 91 is turned on by pushing a corresponding starter switch 97.

FIG. 19 diagrammatically shows an arrangement of a control system of the system, which includes a microcomputer 100 intended for controlling the overall operation of the atomizer system. The microcomputer 100 includes a timer (T) 101 for controlling the timing switch 95 described above. The electromagnetic valves 91, provided one for each of the branching tubes 80*b* of the air outlet unit 50C, are opened/closed in accordance with the control signals received from the microcomputer 100. The treatment periods as prescribed to individual patients may be set by the timing switches 95 on a control panel 102. The periods thus set are input in the microcomputer 100 and stored in a memory therefor. These periods are indicated on the respective indicators 96 on the control panel 102.

When the starter switch 97 associated with an air outlet 50 is pushed following setting a period for the outlet, the switch causes the microcomputer 100 instructs the timer 101 to count down time for the air outlet 50 associated with the switch 97, thereby controlling the electromagnetic valve 91. At the same time, the indicator 96 starts indicating the remaining period of time.

Thus, the electromagnetic valves 91 are conveniently opened and closed to perform inhalation treatment in accordance with the prescriptions for the patients in an automated manner. Moreover, since any one of the electromagnetic valves 91 is opened only after the corresponding starter switch is pushed, the air outlet 50 associated with it may be opened only after the user of the atomizer system is ready for the treatment, thereby carrying out the treatment without failure of treatment due to improper timing of atomization as mentioned above.

It would be noted that the invention may provide air uniformly to each of the air outlets, so that it is possible to effectively perform optimum treatments to a multiplicity of patients.

It would be also noted that steady delivery of low-pressure air is possible by simply installing at each entrance of the branching air outlets of the air outlet unit a regulator for decompressing the high-pressure air. Consequently, inhalation treatments may be carried out to multiple patients in a reliable manner.

Further, because of such dedicated regulators distributed one for each of the branching air outlets, accurate adjustment of pressures for individual air outlets is possible, thereby permitting optimum inhalation treatments to the individual patients.

The atomizer system described herein is also compact and movable, so that it may be utilized anytime and anywhere convenient for a user who needs treatment.

Because the system has a multiplicity of air outlets available for patients, simultaneous treatments of the patients are possible. This is desirable not only in relieving physical and psychological burdens of the patients waiting for treatments, but also relieving the burdens of the nurses who must otherwise attend the patients for a prolonged time.

As noted earlier, although multiple filters are required for cleaning the high-pressure air for the atomizer system, they may be easily replaced as needed, since they are assembled in an integral unit. This helps the nurses maintain sanitary conditions of the system.

Although the presently preferred embodiments of the invention have been described in connection with inhalators for medical treatment, it will be understood that various change may be made within the scope of the appended claims. For example, the invention may be applied to air brushes for painting, gardening sprays for spraying insecticides, and any other similar portable atomizers which can be separated from a main unit carrying a compressor.

What we claim is:

1. An atomizer system comprising:
  a main unit operative to charge a portable unit with an amount of pressurized air, said main unit including:
    an air compressor for generating pressurized air,
    a first pressure accumulation tank for storing a volume of pressurized air generated by said compressor, and
    at least one air tube for conducting said pressurized air from said first pressure accumulation tank to an air outlet; and
  a portable unit which includes:
    a second pressure accumulation tank for accepting an air charge from said first pressure accumulation tank, said second pressure accumulation tank having at least one sealing valve which is detachably connectable to said air outlet of said first pressure accumulation tank,
    a regulator for decompressing the high-pressure air stored in said second pressure accumulation tank to reduce the pressure thereof and to generate low-pressure air having a predetermined pressure, and
    at least one atomizer communicating with said regulator on the downstream side thereof for atomizing liquid by means of said low-pressure air.

2. The atomizer system according to claim 1, wherein said atomizer is removably mounted on said regulator via said valve and said air tube.

3. The atomizer system according to claim 1, wherein said main unit further comprises a filter unit for cleaning said high-pressure air released from said first pressure accumulation tank, thereby providing said second pressure accumulation tank with clean high-pressure air.

4. The atomizer system according to claim 3, wherein said second pressure accumulation tank of said portable unit has a short cylindrical configuration and has on the top thereof said regulator and said atomizer, and a bottom which is separable from the rest of said portable unit.

5. The atomizer system according to claim 4, wherein said filter unit includes:
  a multiplicity of filters for removing different kinds of particles, said filters each having indicator for indicating if they are choked or not;
  a mount in the form of plate for mounting thereon said filters in series; and
  an observation window formed in said mount for monitoring said indicators of said filters, said observation window formed at a position suitable for said observation.

6. The atomizer system according to claim 5, wherein said filter unit includes a dust filter for removing dust in the air, an oil mist filter for removing liquid oil particles, and an odor filter for removing bad odor particles.

7. An atomizer system comprising:
  a movable main unit which includes:
    an air compressor for generating high-pressure air,
    a pressure accumulation tank for storing a volume of high pressure air generated by said compressor,
    at least one regulator for reducing the pressure of said high-pressure air in said pressure accumulation tank to a predetermined low pressure,
    a multiplicity of air outlets communicated with said regulator for delivering said low-pressure air stored in said regulator,
    a multiplicity of valves mounted in said air outlets, one for each air outlet, for controlling the flow of air that passes through said air outlets, and
    at least one atomizer for atomizing liquid by means of said low-pressure air.

8. The atomizer system according to claim 7, wherein said main unit further comprises a removable air filter unit for cleaning said high-pressure air delivered from said pressure accumulation tank, thereby supplying clean high-pressure air from said air outlets.

9. The atomizer system according to claim 8 further comprising a timer which is capable of controlling said valves individually such that said low-pressure air is released from said air outlets for only prescribed periods of time.

10. The atomizer system according to claim 9, wherein said filter unit includes:
  a multiplicity of filters for removing different kinds of particles, said filters each having indicator for indicating if they are choked or not.;
  a mount in the form of plate for mounting thereon said filters in series; and
  an observation window formed in said mount for monitoring said indicators of said filters, said observation window formed at a position suitable for said observation.

11. The atomizer system according to claim 10, wherein said filter unit includes a dust filter for removing dust in the air, an oil mist filter for removing liquid oil particles, and an odor filter for removing bad odor particles.

12. The atomizer system according to claim 11, wherein each of said multiplicity of air outlets is provided with a regulator capable of individually regulating the pressure of the air released from said air outlet.

* * * * *